(12) United States Patent
Ratner

(10) Patent No.: US 11,383,054 B2
(45) Date of Patent: *Jul. 12, 2022

(54) OPTIMIZED BREATHING ASSISTANCE DEVICE

(71) Applicant: MERCURY ENTERPRISES, INC., Clearwater, FL (US)

(72) Inventor: Jeffrey B. Ratner, Pinellas Park, FL (US)

(73) Assignee: MERCURY ENTERPRISES, INC., Clearwater, FL (US)

( * ) Notice: Subject to any disclaimer, the term of this patent is extended or adjusted under 35 U.S.C. 154(b) by 1410 days.

This patent is subject to a terminal disclaimer.

(21) Appl. No.: 15/161,610

(22) Filed: May 23, 2016

(65) Prior Publication Data

US 2016/0325062 A1 Nov. 10, 2016

Related U.S. Application Data

(63) Continuation of application No. 13/592,634, filed on Aug. 23, 2012, now Pat. No. 9,370,635.

(51) Int. Cl.
| | | |
|---|---|---|
| *A61M 16/00* | (2006.01) |
| *A61M 16/08* | (2006.01) |
| *A61M 16/20* | (2006.01) |
| *A61M 16/12* | (2006.01) |
| *A61M 16/04* | (2006.01) |
| *A61M 16/06* | (2006.01) |

(52) U.S. Cl.
CPC .... *A61M 16/0096* (2013.01); *A61M 16/0057* (2013.01); *A61M 16/04* (2013.01); *A61M 16/06* (2013.01); *A61M 16/0816* (2013.01); *A61M 16/0858* (2014.02); *A61M 16/127* (2014.02); *A61M 16/209* (2014.02); *A61M 2016/003* (2013.01); *A61M 2016/0027* (2013.01)

(58) Field of Classification Search
CPC .......... A61M 16/0057; A61M 16/0096; A61M 16/04; A61M 16/06; A61M 16/0816; A61M 16/0858; A61M 16/127; A61M 16/209; A61M 16/0875; A61M 2016/0027; A61M 2016/003; A61M 39/00; A61M 2206/00
USPC ...................................... 128/200.18, 204.25
See application file for complete search history.

(56) References Cited

U.S. PATENT DOCUMENTS

| | | |
|---|---|---|
| 4,495,946 A | 1/1985 | Lerner |
| 4,537,188 A | 8/1985 | Phuc |
| 5,036,847 A | 8/1991 | Boussignac |
| 5,193,532 A | 3/1993 | Moa et al. |
| 5,538,002 A | 7/1996 | Boussignac et al. |
| 6,273,087 B1 | 8/2001 | Boussignac et al. |
| 6,516,801 B2 | 2/2003 | Boussignac |

(Continued)

*Primary Examiner* — Tu A Vo
*Assistant Examiner* — Alexander Morales
(74) *Attorney, Agent, or Firm* — Larson & Larson, PA; Frank Liebenow

(57) ABSTRACT

A breathing assistance device with improved pressure characteristics is capable of providing a high level of CPAP per unit of supplementary respirable gas consumed while maintaining low CPAP fluctuations throughout the breath cycle. The invention also includes a manometer for monitoring pressure and a safety pressure relief valve as additional safety measures against overpressure delivered to a patient. In some embodiments, the device is disposable for one-time or single patient use.

18 Claims, 19 Drawing Sheets

(56) References Cited

U.S. PATENT DOCUMENTS

| | | | |
|---|---|---|---|
| 6,761,172 | B2 | 7/2004 | Boussignac et al. |
| 6,814,075 | B2 | 11/2004 | Boussignac |
| 7,331,344 | B2 | 2/2008 | Foster et al. |
| 7,905,229 | B2 * | 3/2011 | Giroux ................. B05B 7/0869 |
| | | | 128/200.21 |
| 8,561,609 | B2 | 10/2013 | Donovan et al. |
| 8,950,400 | B2 * | 2/2015 | Enk .................... A61M 16/125 |
| | | | 128/204.25 |
| 9,370,635 | B2 * | 6/2016 | Ratner .............. A61M 16/0858 |
| 2005/0066976 | A1 * | 3/2005 | Wondka ............ A61M 16/0009 |
| | | | 128/207.18 |
| 2007/0056587 | A1 | 3/2007 | Travan |
| 2009/0044807 | A1 | 2/2009 | Boussignac |
| 2009/0234325 | A1 * | 9/2009 | Rozenberg ........ A61M 25/0032 |
| | | | 604/514 |
| 2010/0252041 | A1 * | 10/2010 | Kapust .............. A61M 16/0003 |
| | | | 128/204.23 |
| 2010/0252044 | A1 * | 10/2010 | Duquette .......... A61M 16/0677 |
| | | | 128/204.25 |
| 2011/0088696 | A1 | 4/2011 | Ratner |

* cited by examiner

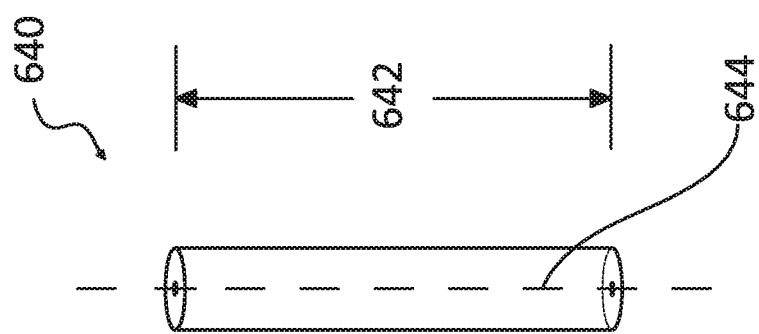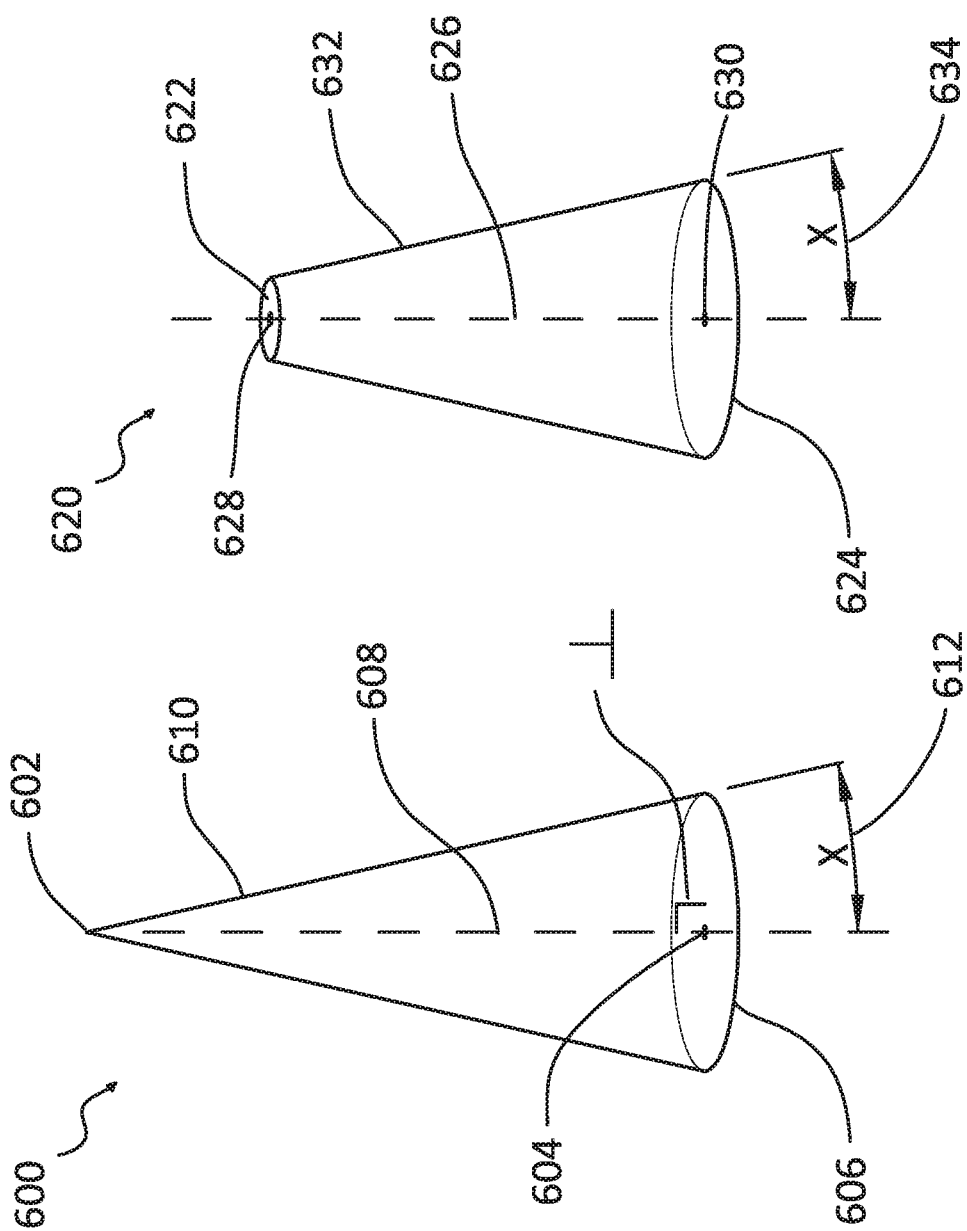

| TABLE 1: PATIENT END OPENING SIZE VS. STATIC PRESSURE ||||||
|---|---|---|---|---|---|
| WALL TYPE | PATIENT END DIAMETER MM | ANGLE OF FRUSTUM WALL | JET ORIFICE DIA. MM | GAS INPUT LPM | STATIC PRESSURE Cm H2O |
| STRAIGHT TUBE | 11.9 | 0 | 0.58 | 12 | 8.5 |
| STRAIGHT TUBE | 12.9 | 0 | 0.58 | 12 | 7.5 |
| STRAIGHT TUBE | 15.8 | 0 | 0.58 | 12 | 5.0 |

FIG. 13

| TABLE 2: PATIENT END OPENING SIZE VS. PRESSURE FLUCTUATION ||
|---|---|
| PATIENT END DIAMETER MM | PRESSURE FLUCTUATION Cm H2O |
| 10.2 | 2.8 |
| 11.0 | 1.5 |
| 12.0 | 1.2 |
| 12.8 | 1.0 |

FIG. 14

| TABLE 3: STEADY CROSS-SECTION WALLS (TUBES) VS. FRUSTUM-SHAPED WALLS OF SAME TYPE | | | | | | | | |
|---|---|---|---|---|---|---|---|---|
| WALL TYPE | PATIENT END OPENING CROSS SECTIONAL AREA SQ MM | WALL ANGLE DEGREES | JET ORIFICE DIAMETER MM | ORIFICE DISTANCE TO PATIENT END OPENING MM | CENTRAL AXIS LENGTH MM | GAS INPUT LPM | STATIC PRESSURE Cm H2O | PRESSURE FLUCTUATION Cm H2O |
| CONICAL FRUSTUM | 95 | 4 | 0.65 | 47 | 47 | 13 | 9.5 | 2.0 |
| CYLINDRICAL STRAIGHT TUBE | 95 | 0 | 0.65 | 47 | 47 | 13 | 11.5 | 7.0 |
| SQUARE FRUSTUM | 95 | 3.5* | 0.65 | 47 | 47 | 13 | 9.8 | 3.0 |
| SQUARE STRAIGHT TUBE | 95 | 0* | 0.65 | 47 | 47 | 13 | 11.5 | 5.5 |
| OCTAGONAL FRUSTUM | 95 | 3.8* | 0.65 | 47 | 47 | 13 | 9.5 | 2.0 |
| OCTAGONAL STRAIGHT TUBE | 95 | 0* | 0.65 | 47 | 47 | 13 | 11.5 | 4.8 |
| *ANGLE MEASURED TO THE CENTER OF THE SIDE AS IN FIGURE 12 | | | | | | | | |

FIG. 15

| TABLE 4: PRESSURE CHARACTERISTICS THROUGH RANGE OF FRUSTUM ANGLES ||||||
|---|---|---|---|---|---|---|
| PATIENT END DIAMETER MM | ORIFICE DISTANCE TO PATIENT END OPENING MM | FRUSTUM ANGLE X | JET ORIFICE DIAMETER MM | GAS INPUT LPM | STATIC PRESSURE Cm H2O | PRESSURE FLUCTUATION Cm H2O |
| 11 | 47 | 0 | 0.65 | 13 | 11.5 | 7.0 |
| 11 | 47 | 2 | 0.65 | 13 | 10.0 | 2.5 |
| 11 | 47 | 3 | 0.65 | 13 | 9.5 | 2.3 |
| 11 | 47 | 4 | 0.65 | 13 | 9.5 | 1.5 |
| 11 | 47 | 5 | 0.65 | 13 | 9.5 | 2.3 |
| 11 | 47 | 6 | 0.65 | 13 | 10.0 | 3.0 |
| 11 | 47 | 7 | 0.65 | 13 | 10.0 | 3.0 |
| 11 | 47 | 8 | 0.65 | 13 | 11.0 | 3.0* |
| 11 | 47 | 9 | 0.65 | 13 | 10.5 | 3.0* |
| * SLIGHT BUFFETING ||||||

FIG. 16

| TABLE 5: TESTS PERFORMED USING 0.58 ORIFICE | | | | | | | |
|---|---|---|---|---|---|---|---|
| WALL TYPE | PATIENT END DIAMETER MM | ANGLE OF FRUSTUM WALL | ORIFICE DISTANCE TO PATIENT END OPENING MM | ORIFICE EXIT DIA. MM | GAS INPUT LPM | STATIC PRESSURE Cm H2O | PRESSURE FLUCTUATION Cm H2O |
| STRAIGHT TUBE | 11.9 | 0 | 56.5 | 0.58 | 12 | 8.5 | 4.0 |
| STRAIGHT TUBE | 12.9 | 0 | 50.0 | 0.58 | 12 | 7.5 | 3.0 |
| STRAIGHT TUBE | 12.9 | 0 | 81.0 | 0.58 | 12 | 7.5 | 2.5 |
| STRAIGHT TUBE | 15.8 | 0 | 72.5 | 0.58 | 12 | 5.0 | 1.5 |
| CONICAL FRUSTUM | 11.0 | 4 | 27.0 | 0.58 | 12 | 9.0 | 4.5 |
| CONICAL FRUSTUM | 11.0 | 4 | 37.0 | 0.58 | 12 | 9.5 | 3.0 |
| CONICAL FRUSTUM | 11.0 | 4 | 47.0 | 0.58 | 12 | 9.3 | 3.0 |
| CONICAL FRUSTUM | 11.0 | 4 | 57.0 | 0.58 | 12 | 8.0 | 1.0 |
| CONICAL FRUSTUM | 11.0 | 4 | 67.0 | 0.58 | 12 | 7.5 | 2.5 |
| CONICAL FRUSTUM | 15.8 | 4 | 27.0 | 0.58 | 12 | 4.5 | 0.8 |
| CONICAL FRUSTUM | 15.8 | 4 | 37.0 | 0.58 | 12 | 4.5 | 1.0 |
| CONICAL FRUSTUM | 15.8 | 4 | 47.0 | 0.58 | 12 | 4.8 | 2.3 |
| CONICAL FRUSTUM | 15.8 | 4 | 57.0 | 0.58 | 12 | 4.8 | 1.5 |
| CONICAL FRUSTUM | 15.8 | 4 | 67.0 | 0.58 | 12 | 4.3 | 1.5 |
| CONICAL FRUSTUM | 11.8 | 4 | 77.5 | 0.58 | 12 | 5.5 | 0.5 |

FIG. 17

| TABLE 6: TESTS PERFORMED USING 0.65 ORIFICE ||||||||
| WALL TYPE | PATIENT END DIAMETER MM | ANGLE OF FRUSTUM WALL | ORIFICE DISTANCE TO PATIENT END OPENING MM | ORIFICE EXIT DIA. MM | GAS INPUT LPM | STATIC PRESSURE Cm H2O | PRESSURE FLUCTUATION Cm H2O |
|---|---|---|---|---|---|---|---|
| STRAIGHT TUBE | 11.9 | 0 | 56.5 | 0.65 | 13 | 9.5 | 3.5 |
| STRAIGHT TUBE | 12.9 | 0 | 50.0 | 0.65 | 13 | 8.0 | 3.0 |
| STRAIGHT TUBE | 12.9 | 0 | 81.0 | 0.65 | 13 | 8.0 | 3.0 |
| STRAIGHT TUBE | 15.8 | 0 | 72.5 | 0.65 | 13 | 5.0 | 1.5 |
| CONICAL FRUSTUM | 11.0 | 4 | 27.0 | 0.65 | 13 | 9.5 | 4.0 |
| CONICAL FRUSTUM | 11.0 | 4 | 37.0 | 0.65 | 13 | 10.0 | 2.0 |
| CONICAL FRUSTUM | 11.0 | 4 | 47.0 | 0.65 | 13 | 9.5 | 1.5 |
| CONICAL FRUSTUM | 11.0 | 4 | 57.0 | 0.65 | 13 | 8.5 | 2.5 |
| CONICAL FRUSTUM | 11.0 | 4 | 67.0 | 0.65 | 13 | 8.0 | 2.5 |
| CONICAL FRUSTUM | 15.8 | 4 | 27.0 | 0.65 | 13 | 5.3 | 0.5 |
| CONICAL FRUSTUM | 15.8 | 4 | 37.0 | 0.65 | 13 | 4.8 | 1.0 |
| CONICAL FRUSTUM | 15.8 | 4 | 47.0 | 0.65 | 13 | 5.0 | 1.5 |
| CONICAL FRUSTUM | 15.8 | 4 | 57.0 | 0.65 | 13 | 5.0 | 2.0 |
| CONICAL FRUSTUM | 15.8 | 4 | 67.0 | 0.65 | 13 | 4.8 | 1.8 |
| CONICAL FRUSTUM | 11.8 | 4 | 77.5 | 0.65 | 13 | 6.5 | 1.5 |

FIG. 18

| TABLE 7: TESTS PERFORMED USING 0.79 ORIFICE | | | | | | | |
|---|---|---|---|---|---|---|---|
| WALL TYPE | PATIENT END DIAMETER MM | ANGLE OF FRUSTUM WALL | ORIFICE DISTANCE TO PATIENT END OPENING MM | ORIFICE EXIT DIA. MM | GAS INPUT LPM | STATIC PRESSURE Cm H2O | PRESSURE FLUCTUATION Cm H2O |
| STRAIGHT TUBE | 11.9 | 0 | 56.5 | 0.79 | 18 | 13.5 | 5.0 |
| STRAIGHT TUBE | 12.9 | 0 | 50.0 | 0.79 | 18 | 11.0 | 4.0 |
| STRAIGHT TUBE | 12.9 | 0 | 81.0 | 0.79 | 18 | 11.0 | 3.0 |
| STRAIGHT TUBE | 15.8 | 0 | 72.5 | 0.79 | 18 | 7.0 | 2.5 |
| CONICAL FRUSTUM | 11.0 | 4 | 27.0 | 0.79 | 18 | 13.5 | 5.0 |
| CONICAL FRUSTUM | 11.0 | 4 | 37.0 | 0.79 | 18 | 14.0 | 3.5 |
| CONICAL FRUSTUM | 11.0 | 4 | 47.0 | 0.79 | 18 | 13.0 | 1.5 |
| CONICAL FRUSTUM | 11.0 | 4 | 57.0 | 0.79 | 18 | 11.5 | 1.5 |
| CONICAL FRUSTUM | 11.0 | 4 | 67.0 | 0.79 | 18 | 11.0 | 2.0 |
| CONICAL FRUSTUM | 15.8 | 4 | 27.0 | 0.79 | 18 | 6.8 | 0.8 |
| CONICAL FRUSTUM | 15.8 | 4 | 37.0 | 0.79 | 18 | 6.8 | 2.0 |
| CONICAL FRUSTUM | 15.8 | 4 | 47.0 | 0.79 | 18 | 7.0 | 2.0 |
| CONICAL FRUSTUM | 15.8 | 4 | 57.0 | 0.79 | 18 | 6.8 | 2.5 |
| CONICAL FRUSTUM | 15.8 | 4 | 67.0 | 0.79 | 18 | 6.5 | 1.5 |
| CONICAL FRUSTUM | 11.8 | 4 | 77.5 | 0.79 | 18 | 9 | 2.5 |

FIG. 19

| TABLE 8: STATIC PERFORMANCE COMPARISON OF COMMONLY USED CPAP DEVICES | | |
|---|---|---|
| DEVICE | GAS INPUT LPM | STATIC PRESSURE Cm H2O |
| BOUSSIGNAC CPAP DEVICE | 25.0 | 6.8* |
| MERCURY FLOW SAFE CPAP DEVICE | 25.0 | 8.9 |
| APPLICANT'S INVENTION | 12.5 | 8.9 |
| BOUSSIGNAC CPAP DEVICE | 29.5 | 10.0 |
| MERCURY FLOW SAFE CPAP DEVICE | 25.9 | 10.0 |
| APPLICANT'S INVENTION | 13.6 | 10.0 |
| *BOUSSIGNAC DEVICE TESTED DID NOT MEET ADVERTISED SPECIFICATION | | |

FIG. 20

| TABLE 9: DYNAMIC PERFORMANCE COMPARISON OF COMMONLY USED CPAP DEVICES | | | |
|---|---|---|---|
| DEVICE | GAS INPUT LPM | STATIC PRESSURE Cm H2O | PRESSURE FLUCTUATION Cm H2O |
| BOUSSIGNAC CPAP DEVICE | 29.5 | 10.0 | 3.5 |
| MERCURY FLOW SAFE CPAP DEVICE | 25.9 | 10.0 | 3.8 |
| APPLICANT'S INVENTION | 13.6 | 10.0 | 1.7 |

FIG. 21

OPTIMIZED BREATHING ASSISTANCE DEVICE

CROSS-REFERENCE TO RELATED APPLICATION

This application is a continuation of U.S. patent application Ser. No. 13/592,634, filed Aug. 23, 2012, the disclosure of which is hereby incorporated by reference.

FIELD

The present invention relates to the field of breathing assistance devices.

BACKGROUND

Breathing aids or breathing assistance devices are well known in the art. Numerous devices have been disclosed which are designed to assist a patient who is having difficulty breathing. These devices often supply supplemental oxygen at a concentration higher than that in the atmosphere, and often under pressure, as a means of promoting improved respiration and/or improved oxygen absorption. Further, numerous breathing assistance devices which are designed to provide a continuous positive airway pressure (CPAP) have likewise been disclosed.

For example, U.S. Pat. No. 5,036,847, by Boussignac et al., discloses a breathing aid comprising a tubular main channel through which respiration occurs, with one end open to the atmosphere and at least one additional auxiliary channel opening into the main channel through which supplemental pressurized respirable gas (e.g. oxygen) is provided to the patient. The device produces a continuous positive airway pressure (CPAP). The invention of U.S. Pat. No. 5,036,847 also comprises a deflection face as a means to deflect the jet(s) of respirable gas exiting the auxiliary channel(s) towards the center of the main channel so that the jet(s) of respirable gas does not directly strike the patient's mucous membranes. Further, the disclosure also provides for an additional channel which opens into the distal (patient) end face of the tube and which may be connected to a pressure measurement device as well as a safety pressure relief device (comprising perforations through the main tube in conjunction with a safety sleeve) to relieve pressure within the main tube in the event that the internal pressure becomes too high.

U.S. Pat. Nos. 5,538,002, 6,273,087, 6,363,935, 6,516, 801, 6,761,172, and 6,814,075, as well as U.S. Patent Application No. 2009/0044807 A1, all by Boussignac (et al.), each likewise disclose similar inventions with various additional features. Many of these provide for a calibrated pressure relief valve in the proximal region of the main tube to relieve pressure in the main channel in the case of overpressure. Most of these require that the auxiliary channel(s) open into the main tube near ("close to," "in proximity of," "in the vicinity of") the distal (i.e. patient) end of the device.

As another example, U.S. Pat. No. 5,193,532 by Moa et al., discloses a breathing assistance device which produces a continuous positive airway pressure by means of an ejector action due to the influx of supplemental respirable gas into a breathing channel through an inlet channel. This device, like the Boussignac devices referred to above, also exhibits a branch channel open to the atmosphere and is therefore not a closed circuit, ventilator type CPAP system. Further, in this device the breathing channel (first branch channel) and the exhaust channel (second branch channel) are not linearly aligned but rather form an angle of 30 to 50 degrees with one another.

U.S. Pat. No. 7,331,344, by Foster et al., discloses yet another example of a "breathing device" wherein supplemental respirable gas is provided into a breathing channel through an inlet channel. As in the above examples, the exhaust channel in this invention is open to the atmosphere. And here, once again, the breathing channel and exhaust channel are not collinear but rather form an oblique angle with one another. The inlet channel is laterally offset from the breathing channel so as to introduce supplemental respirable gas in such a manner that a "bypass" occurs, whereby some portion of the supplemental respirable gas goes directly to the exhaust channel. According to the author, "It has been recognized that the phenomena of jet bypass, whereby a proportion of the fresh gas supplied to the patient passes directly out of the exhaust tube is crucial in giving the low added work of breathing." Col. 1, Lines 38-41.

U.S. Pat Application No. 20110088696, by Ratner, discloses a disposable breathing assistance device with manometer for monitoring the pressure within the device, a safety pressure relief valve and a specialized supplementary respirable gas inlet combined with a specialized main channel which provides improved pressure characteristics.

Each of the above-described devices provide an exhaust channel open to the atmosphere yet provide a continuous positive airway pressure at the user end of the device. The use of continuous positive airway pressure both forces gas into the lungs during inhalation and forces the patient to exhale against pressurized gas during exhalation which may prevent the alveoli from collapsing. It has been found that in many cases, the use of such a CPAP device is of great assistance to patients experiencing breathing difficulties.

SUMMARY

The applicant has discovered numerous disadvantages to previously disclosed inventions.

First, applicant has discovered that many previously disclosed devices do not use supplementary respirable gas as efficiently as is both possible and desirable. CPAP is often applied in situations where a limited supplementary respirable gas supply is available; for example where portable oxygen containers are used on site in emergency situations. The length of time a CPAP device can be supplied using a given portable supplementary respirable gas tank is dependent upon the rate at which the supplementary respirable gas is used. Therefore devices that unnecessarily use supplementary respirable gas at faster rates are clearly less desirable in such situations. Whereas the ability to generate the same effective CPAP using a reduced quantity of supplementary respirable gas is desirable since it extends the length of time a given supplementary respirable gas supply can serve effectively. Additionally, there is an advantage to conserving supplementary respirable gas in general as a means of cost containment, even in situations where the supplementary respirable gas supply is not so strictly limited as it is in the examples above. The applicant's design provides the same effective CPAP as many previously disclosed devices while dramatically reducing the supplementary respirable gas requirements to accomplish this effect.

A second disadvantage to previously disclosed devices is that typically the CPAP pressure inside currently commonly used CPAP systems will increase significantly during patient exhalation and decrease significantly during patient inhalation. In CPAP application, this type of pressure fluctuation is considered to be associated with an increased work of breathing, i.e. larger fluctuations of internal pressure making breathing more difficult for the patient whose breathing is already distressed. For this reason, there is an advantage in reducing the amplitude of this type of pressure fluctuation. Experimentation involving variation of multiple parameters was undertaken by applicant in order to optimize the function and achieve the desired effect. As a result, applicant's invention not only provides for effective CPAP with reduced supplementary gas requirements, but also addresses the fluctuation issue as well, and provides a stable, consistent CPAP pressure with minimal fluctuation throughout the breathing cycle. These are 2 very desirable qualities in a breathing assistance device.

Additionally, the disclosed device provides for the attachment of a manometer for internal pressure measurement and may optionally comprise a calibrated pressure relief valve for added safety against overpressure and its dangers to the patient. Further, the entire device may be made to be completely disposable for one time or single patient use.

BRIEF DESCRIPTION OF THE DRAWINGS

FIGS. 6A, 6B, and 6C compare a right circular cone, a right circular conic frustum, and a cylindrical tube and illustrates the measurement of the angle of the frustum wall in relation to the central axis.

FIG. 13—Table 1 illustrates the relationship between Static Pressure and Patient End Opening Size.

FIG. 14—Table 2 illustrates the relationship between Pressure Fluctuation and Patient End Opening Size.

FIG. 15—Table 3 compares Tubular structures with Frustum-shaped Walls.

FIG. 16—Table 4 illustrates the relationship between Frustum Wall Angle and Pressure Characteristics.

FIG. 17—Table 5 tabulates examples of experimental results obtained using a 0.58 mm diameter jet orifice.

FIG. 18—Table 6 tabulates examples of experimental results obtained using a 0.65 mm diameter jet orifice.

FIG. 19—Table 7 tabulates examples of experimental results obtained using a 0.79 mm diameter jet orifice.

FIG. 20—Table 8 compares Static Pressure produced vs. LPM supplementary gas flow in applicant's invention and 2 prior art devices.

FIG. 21—Table 9 compares Pressure Fluctuation in applicant's invention with 2 prior art devices.

REFERENCE NUMERALS IN DRAWINGS

Figure 1:
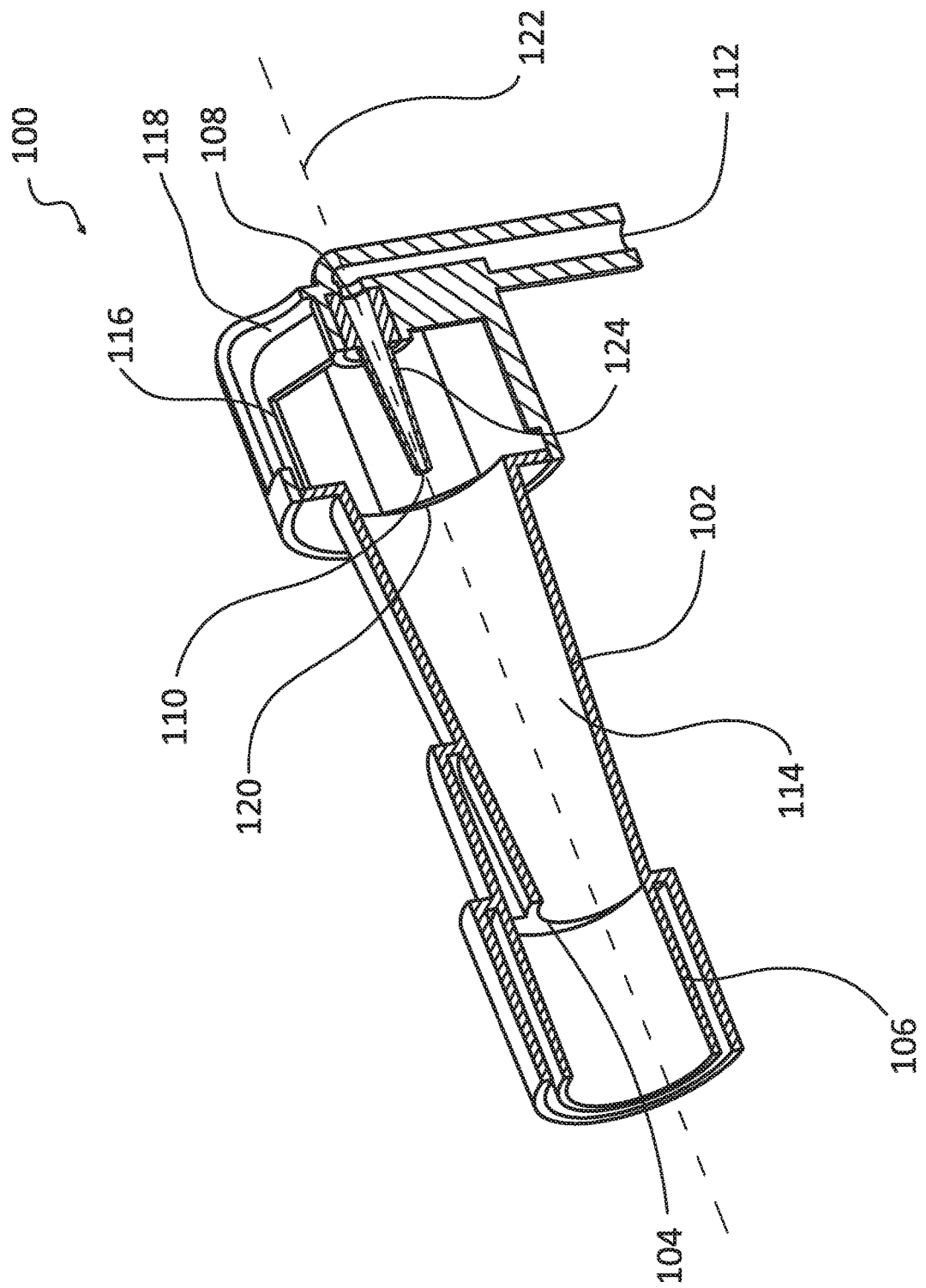
FIG. 1 shows an isometric section view of an example of a breathing assistance device according to the present invention

100 An example of a breathing assistance device according to the present invention
102 Frustum-shaped wall
104 Patient End Opening
106 Connector
108 Jet
110 Jet Orifice
112 Gas Input Port
114 Interior Space
116 Atmospheric Opening
118 Endcap
120 Wide End of Frustum-shaped Wall
122 Central Axis of Frustum-Shaped Wall
124 Frustum-Shaped Wall of Jet
300 Test Fixture
302 Linear Slide Controlled by Stepper Motor
304 3-Liter Syringe
306 Computer
308 Breathing Assistance Device
310 Pressure Gauge
312 Syringe/Breathing Assistance Device Junction
314 Supplementary Gas Tank
316 Flow Meter
318 Connective Tubing
400 Regular Square Pyramid
420 Frustum of Regular Square Pyramid
422 Narrow End/Top Face of Frustum
424 Wide End/Bottom Face of Frustum
426 Central Axis of Frustum
428 Geometric Center of Square Top Face of Frustum
430 Geometric Center of Square Bottom Face of Frustum
440 Square Tube
442 Length of Square Tube
444 Central Axis of Square Tube
500 Regular Octagonal Pyramid
520 Frustum of Regular Octagonal Pyramid
522 Narrow End/Top Face of Frustum
524 Wide End/Bottom Face of Frustum
526 Central Axis of Frustum
528 Geometric Center of Octagonal Top Face of Frustum
530 Geometric Center of Octagonal Bottom Face of Frustum
540 Octagonal Tube
542 Length of Octagonal Tube
544 Central Axis of Octagonal Tube
600 Right Circular Cone
602 Vertex of Cone
604 Center of Base of Cone
606 Base of Cone
608 Central Axis of Cone
610 Wall of Cone
612 Angle Between Wall of Cone and Central Axis
620 Frustum of Right Circular Cone
622 Narrow End/Top Face of Frustum
624 Wide End/Bottom Face of Frustum
626 Central Axis of Frustum 628 Geometric Center of Top Face of Frustum
630 Geometric Center of Bottom Face of Frustum
632 Wall of Frustum
634 Angle between Wall of Frustum and Central Axis
640 Cylindrical Tube
642 Length of Cylindrical Tube
644 Central Axis of Cylindrical Tube
700 An example of a breathing assistance device according to the present invention with manometer and pressure relief valve.
702 Manometer
704 Pop-off Safety Relief Valve
706 Manometer Port
708 Connector
710 Pressure Release Vent
712 Atmospheric Opening
714 Endcap
716 Gas Input Port
802 Pressure Measurement Channel
804 Throughhole
806 Frustum-shaped Wall
808 Pop-off Safety Relief Valve Housing
810 Endcap of Pop-off Safety Relief Valve
812 Ball of Pop-off Safety Relief Valve
814 Spring of Pop-off Safety Relief Valve
816 Interior Space
818 Jet
820 Patient End Opening
822 Jet Orifice
1000 Irregular Heptagonal Pyramid
1002 Vertex of Pyramid
1004 Centroid of Base of Pyramid
1006 Base of Pyramid
1008 Central Axis of Pyramid
1020 Frustum of Irregular Heptagonal Pyramid
1022 Central Axis of Frustum
1024 Narrow End/Top Face of Frustum
1026 Wide End/Bottom Face of Frustum
1028 Centroid of Heptagonal Top Face of Frustum
1030 Centroid of Heptagonal Bottom Face of Frustum
1040 Irregular Heptagonal Tube
1042 Top Face of Irregular Heptagonal Tube
1044 Bottom Face of Irregular Heptagonal Tube
1046 Side Face of Irregular Heptagonal Tube
1048 Central Axis of Irregular Heptagonal Tube
1100 Right Circular Cone
1102 Central Axis of Cone
1104 Bottom Face of Cone
1106 Wall of Cone
1108 Angle Between Wall of Cone and Central Axis
1120 Angled Frustum of Cone
1122 Top Face of Angled Frustum
1124 Bottom Face of Angled Frustum
1126 Central Axis
1128 Circular Cross-Section Perpendicular to Central Axis of Cone and Tangent to Top Face of Cone Portion
1130 Circular Cross-Section Perpendicular to Central Axis of Cone and Tangent to Bottom Face of Cone Portion
1132 Top Portion
1134 Middle Portion
1136 Bottom Portion
1140 Portion of Cone
1142 Circular Cross-Section Perpendicular to Central Axis of Cone and Tangent to Top Face of Cone Portion
1144 Circular Cross-Section Perpendicular to Central Axis of Cone and Tangent to Bottom Face of Cone Portion
1146 Top Portion
1148 Middle Portion
1150 Bottom Portion
1152 Top Face of Cone Portion
1154 Bottom Face of Cone Portion
1200 Frustum of Regular Square Pyramid
1202 Square Top Face of Frustum
1204 Center of Top Face
1206 Square Bottom Face of Frustum
1208 Center of Bottom Face
1210 Central Axis of Frustum
1212 Side Face of Frustum
1214 Line Drawn Down Center of Side Face of Frustum
1216 Angle Between Center of Side Face and Central Axis
1218 Edge Between Side Faces
1220 Angle Between Edge and Central Axis

DETAILED DESCRIPTION

The present invention is a breathing assistance device. (See FIGS. 1 and 2 for a cross-section and isometric view of an example of the present invention.) The device generally comprises a body exhibiting a concave substantially frustum-shaped interior wall. The substantially frustum-shaped interior wall defines an interior space. The narrow end of the frustum forms the patient end opening through which respired gas will pass during the breathing cycle. The patient end opening preferably leads to a connector that is adapted to be engaged directly with a patient's breathing tract (e.g. by formation into an endotracheal tube) or adapted to be engaged indirectly with a patient's breathing tract (e.g. via connection to a mask). The device further comprises a jet which, in use, directs supplementary respirable gas from a supplementary respirable gas source, such as an oxygen tank, through the interior space towards the patient end opening. The body further has openings to the atmosphere which allow fluid communication of gas between the interior space and the atmosphere. The device further comprises an input port for connection to a source of supplementary respirable gas, such as concentrated oxygen, to supply the jet.

In use, the jet creates an increased pressure, particularly near the patient end opening and beyond, into the patient's airway. Upon inhalation, the patient breathes in supplementary respirable gas that enters the interior space though the jet orifice as well as atmospheric air that is drawn into the interior space though the atmospheric openings in the body of the device. Upon exhalation, the expired air exits from the patient through the connector, out through the patient end opening, out through the interior space, and finally exiting the device through the openings to the atmosphere.

By varying each the angle of the frustum-shaped interior wall in relation to the central axis of the device, the type of frustum-shaped wall, the size of the patient end opening, the distance of the jet from the patient end opening, the positioning of the jet in relation to the central axis, and the size of the jet orifice through which respirable gas is injected, applicant has optimized the device to provide desirable pressure characteristics including that both:

1) The amount of supplementary respirable gas required to achieve a given pressure at the patient end of the device is dramatically reduced as compared to prior art devices; and 2) The amplitudes of pressure fluctuations within the device throughout the breathing cycle, are dramatically reduced as compared with pressure fluctuations within prior art devices, resulting in a desirable reduction in the patient's work of breathing as compared to the work of breathing required to use prior art devices.

The invention may also optionally comprise a manometer engaged with the interior space so as to measure the pressure within the interior space, and which preferably continuously provides a conveniently discernable current indication of this pressure. The invention may also optionally comprise a safety pressure relief valve designed to relieve pressure from the interior space should the pressure become excessive.

In order to optimize supplementary respirable gas utilization within a CPAP device, applicant undertook experimentation with various breathing aid prototypes of differing internal architectural designs. The basic design of each of the prototypes comprised a jet of respirable gas directed towards patient end openings that were set in different architectural surroundings in an attempt to optimize the gas flow through the opening, as well as the pressure characteristics around the opening, for CPAP purposes.

Figure 3:
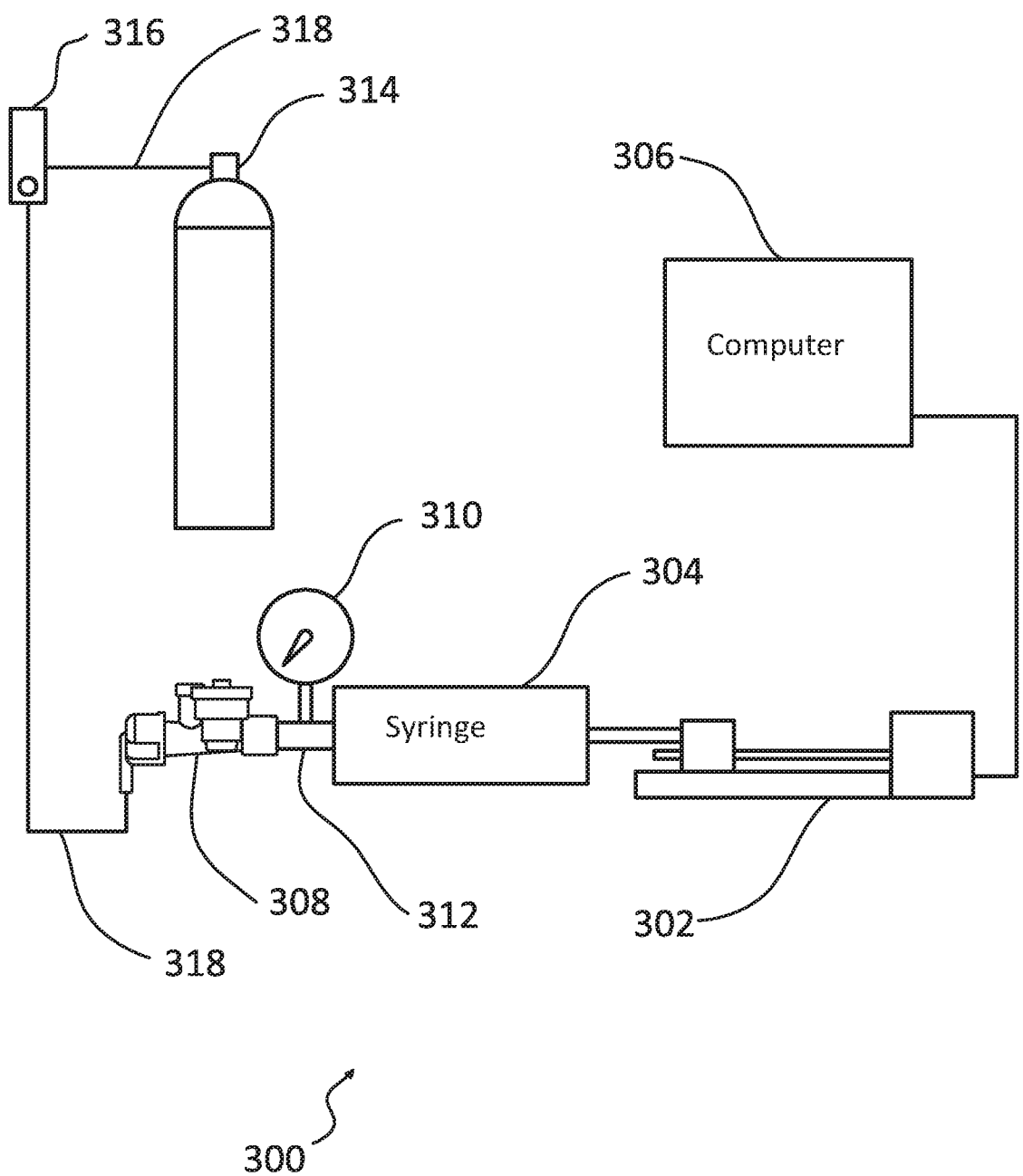
FIG. 3 shows a diagram of the test fixture.

Applicant created a test fixture to reproduce the dynamic breathing pattern of a distressed adult patient with a tidal volume of 1720 ml, an I:E (inspiratory time to expiratory time) ratio of 1:1 and a breath rate of 19 breaths per minute (BPM). Referring to FIG. 3, a representation of the test fixture (300) is shown. The test fixture utilizes a linear slide controlled by a stepper motor (302) to alternately pump air out of and draw air into a 3-liter syringe (304). A computer (306) controls the stepper motor/linear slide apparatus (302) to produce the desired pumping pattern. The syringe (304) is engaged with the patient end of the breathing assistance device (308) to be tested. A pressure gauge (310) is interposed at the junction (312) between the syringe (304) and the patient end of the breathing assistance device (308), allowing for constant immediate monitoring of the pressure within the apparatus at a point approximately 32 mm outside the patient end connector of the breathing assistance device (308) being tested. This point might be equivalent to just inside a face mask and outside a patient's mouth, or within the external end of an endotracheal tube, etc. depending upon the patient interface arrangement utilized. A supplementary gas tank (314) and an adjustable flow meter (316) are connected via tubing (318) to the gas input port of the breathing assistance device (308) to be tested.

Experimental prototypes were tested on this test fixture (300) in a static condition (i.e. stepper motor off and slide stationary, analogous to patient not breathing) and a dynamic condition (i.e. stepper motor on and continuously pumping syringe via slide, analogous to patient breathing). In the static condition, the static CPAP pressure generated was recorded in cm H2O for each LPM (liters per minute) gas input flow tested. In the dynamic condition, the peak high CPAP pressure was recorded during the exhale phase and the peak low CPAP pressure was recorded during the inhale phase in cm $H_2O$ for each LPM gas input flow tested. The pressure fluctuation (delta) is calculated by subtracting the peak low pressure from the peak high pressure.

In attempting to optimize the function of the breathing assistance device, certain limitations are immediately placed upon the preferable size for the patient end opening of the device, as well as upon the cross-sectional area of the entire gas flow path, through which all gas inspired and expired by the patient will pass. As an upper limit it is preferable that the patient end opening not be larger than a hole, 15.8 mm in diameter. 15.8 mm diameter is the internal size of universally used connectors (to masks, etc.) and so the airflow path through any apparatus connected to such a universal connector must ultimately be limited to a maximum of approximately 196 square millimeters (equivalent to cross-section of 15.8 mm diameter hole) at the connection point to such a universal connector. As a lower limit, the patient end opening cannot be so small that it prevents the patient from readily inhaling and exhaling a sufficient amount of gas through it. If the opening becomes too small, the patient is unable to move a sufficient volume of gas through it to support respiration requirements. This principle apples to the most constricted regions of the gas flow path as well; the patient must be able to inhale and exhale a sufficient volume of gas through the device to support respiratory needs and too great a restriction at any point in the gas flow path can prevent these needs from being met. In order to accommodate any size adult patient and the corresponding varying oxygen requirements, applicant suggests that the lower safe limit for the size of the patient end opening is a cross-sectional area of approximately 63 square millimeters (the equivalent cross-sectional of a round hole of 9 mm diameter). Below this size, it becomes questionable whether an adult patient will be able to breathe a sufficient volume of gas though the opening. Similar limitations apply to the entire gas flow path; in a device designed for adult use, no portion of the gas flow path should have a cross-sectional area of less than approximately 63 square millimeters. However, it might be preferable to consider a smaller patient end opening size or a more constricted gas flow path when designing devices specifically for use with infants, small children, etc.

With minimal experimentation, it is clear that for a given flow of injected supplementary respirable gas, a higher static pressure is achieved at the measurement point as the patient end opening decreases in size. Referring to FIG. 13, Table 1, the relationship between static pressure and patient end opening size is illustrated. In attempting to optimize usage of supplementary respirable gas, use of the smallest safe patient end opening size is therefore indicated if maximizing static pressure were the only factor to consider.

However, experimentation in the dynamic mode also revealed, as expected, that the smaller the patient end opening, the greater the fluctuation of pressure at the measurement location throughout the breathing cycle. Referring to FIG. 14, Table 2, the relationship between pressure fluctuation and patient end opening size is illustrated. We can see from table 2, that a large increase in pressure fluctuation occurs as we reduce the size of the patient end opening. The difference in moving from an 11 mm diameter opening to a 10.2 mm diameter opening is an increase of approximately 86% in the fluctuation delta. Therefore, in order to achieve a desirable balance emphasizing both minimizing supplementary respirable gas usage and minimizing pressure fluctuations throughout the breathing cycle, as well as to afford a margin of certainty that enough gas can pass through the opening to support easy adult respiration, applicant has chosen a round opening of 11 mm in diameter as preferable for his examples below, not so small as to deprive the patient of sufficient respirable gas or to dramatically increase pressure fluctuations but small enough to significantly reduce consumption of the available supplementary respirable gas supply.

Experimentation with the architecture around the patient end opening revealed that devices utilizing a frustum-shaped wall surrounding the patient end opening yield more desirable pressure characteristics than devices utilizing the respective tubular conduit leading to the patient end opening. According to one definition, a tube is a long hollow and typically cylindrical object, used for the passage of fluids or as a container. Applicant means to include hollow conduits with non-cylindrical (e.g. square, octagonal, etc.) interiors in the definition of the word "tube." "Tube" is here meant to include any shape conduit with substantially steady internal cross-sectional area and internal shape throughout its length.

A regular pyramid is one whose base is a regular polygon whose center coincides with the foot of the perpendicular dropped from the vertex to the base. A frustum of a regular pyramid is a portion of the regular pyramid included between the base and a section parallel to the base.

A right circular cone is one whose base is a circle whose center coincides with the foot of the perpendicular dropped from the vertex to the base. A frustum of a right circular cone is a portion of the right circular cone included between the base and a section parallel to the base.

Applicant is herein defining "concave frustum-shaped wall" to mean a wall with the shape of the inner surface of a frustum. The outer surface of the frustum wall would be considered to be convex by this definition and is not what is being referenced. The body of applicant's device exhibits a wall that has the shape of the inner concave surface of a frustum. The shape of the exterior surface of this same wall has little bearing on the airflow and pressure characteristics within and through the device.

Figure 4C:
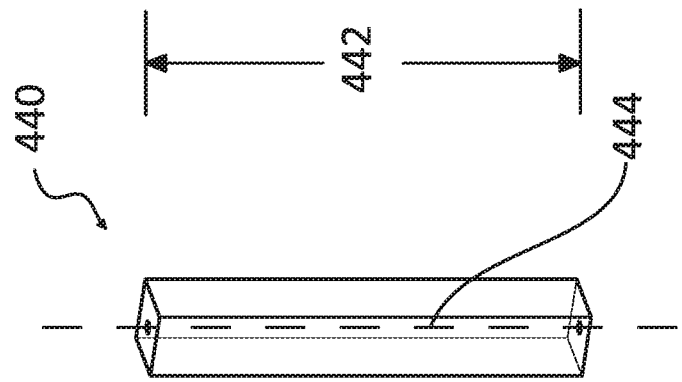
FIGS. 4A, 4B, and 4C compare a regular square pyramid, a regular square pyramidal frustum and a square tube.
Figure 4B:
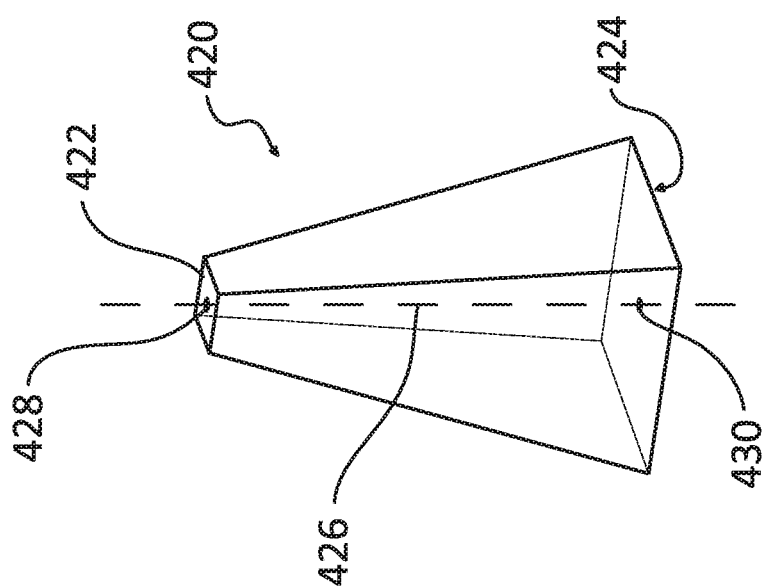
Figure 4A:
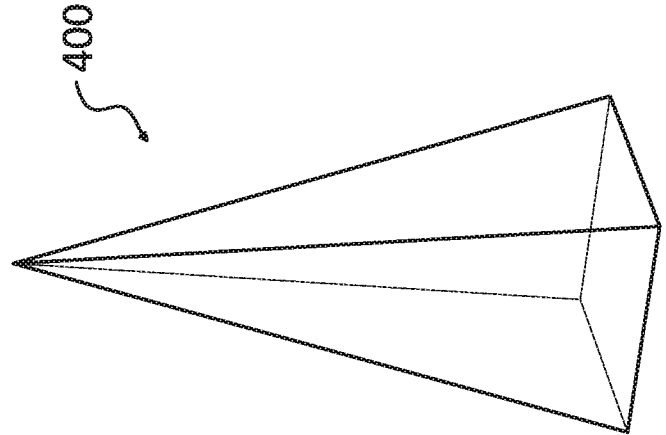

Referring to FIG. 4A, a regular square pyramid (400) is shown. Referring to FIG. 4B, a frustum (420) of the same regular square pyramid is shown. The square pyramidal frustum (420) has narrow end (422), wide end (424) and a central axis (426) passing through the geometric centers (428, 430) of the top and bottom square faces (422, 424). Referring to FIG. 4C, a square tube is shown. The narrow end (422) of the frustum (420) has the same cross-sectional area as the respective square tube (440) has along its entire length (442).

Figure 5C:
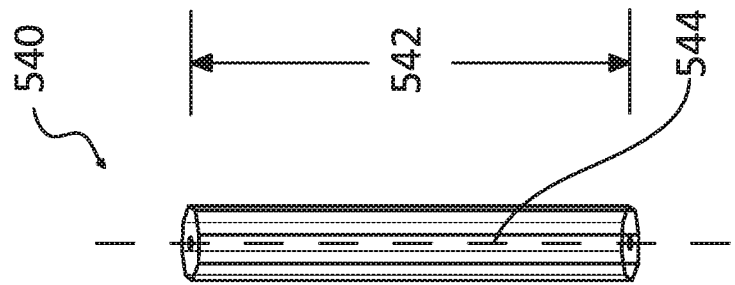
FIGS. 5A, 5B, and 5C compare a regular octagonal pyramid, a regular octagonal pyramidal frustum, and a regular octagonal tube.
Figure 5B:
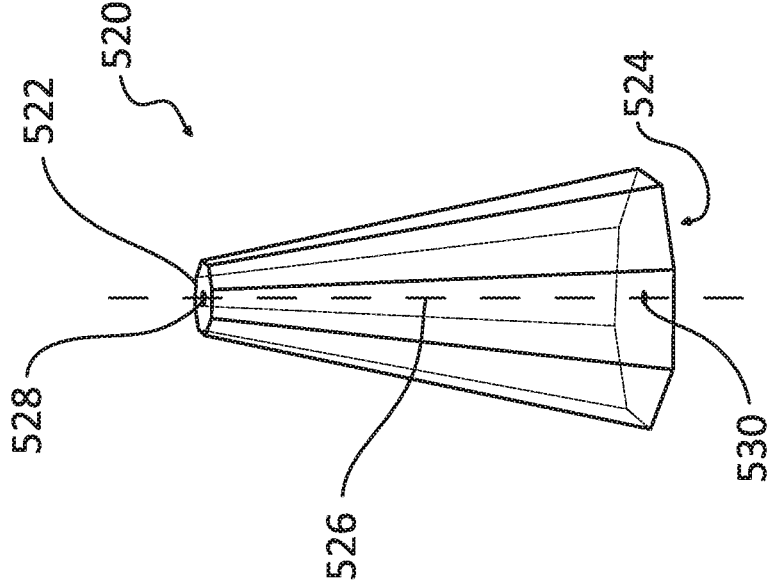
Figure 5A:
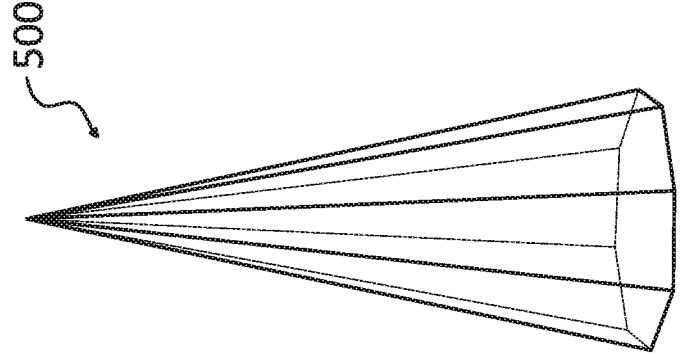

Referring to FIG. 5A, a regular octagonal pyramid (500) is shown. Referring to FIG. 5B, a frustum (520) of the same regular octagonal pyramid is shown. The octagonal pyramidal frustum (520) has narrow end (522), wide end (524) and a central axis (526) passing through the geometric centers (528, 530) of the top and bottom octagonal faces (522, 524). Referring to FIG. 5C, an octagonal tube (540) is shown. The narrow end (522) of the frustum (520) has the same cross-sectional area as the respective octagonal tube (540) has along its entire length (542).

Referring to FIG. 15, Table 3, examples of results of experiments comparing tubular structures with frustum-shaped walls are tabulated. A device utilizing a conical frustum-shaped wall surrounding the patient end opening yielded more desirable pressure characteristics as compared with the corresponding device utilizing an even-diameter, cylindrical tubular conduit leading to the patient end opening. Similar improvements in desired characteristics were obtained when using a regular square pyramidal frustum-shaped wall as compared to its counterpart square tubular wall with steady cross-sectional area throughout its length. Likewise, improvements in desired characteristics were obtained when utilizing a regular octagonal pyramidal frustum-shaped wall as compared to the respective octagonal tubular wall.

After determining that a frustum-shaped wall yielded improved characteristics as compared with a tubular wall (defining an even cross-sectional area throughout its length), experimentation was then undertaken to determine the optimum angle of the frustum-shaped wall in relation to its central axis in order to yield the most desirable pressure characteristics. Referring to FIG. 6A, a right circular cone (600) is shown. The apex (602) is located directly above the center (604) of the circular base (606) of the cone (600). The central axis (608) is an imaginary line through the apex of the cone straight down through the center (604) of the base (606). The central axis forms angle x (612) with the wall of the cone (610). (All cones and frusta depicted for mathematical explanatory purposes have been represented in their standard upright position for ease of understanding. In use, the frustum-shaped wall of the device would most likely not be in this orientation.)

Referring to FIG. 6B, a frustum (620) of the same right circular cone is shown. The right circular conic frustum (620) has narrow end (622), wide end (624) and a central axis (626) passing through the geometric centers (628, 630) of the top and bottom circular faces (622, 624). Referring to FIG. 6C, a cylindrical tube (640) is shown. The narrow end (622) of the frustum (620) has the same cross-sectional area as the respective cylindrical tube (640) has along its entire length (642). Again, as with the cone (600), the wall (632) of the frustum (620) makes angle x (634) with the central axis (626).

Utilizing a conical frustum-shaped wall surrounding an 11 mm diameter circular patient end opening and injecting supplementary respirable gas through a 0.65 mm diameter circular jet orifice, located at 47 mm along the central axis from the patient end opening, the pressure characteristics were tested through a range of frustum angles (i.e. the size of frustum angle x, as illustrated in FIG. 6B, was varied and devices comprising the resulting frustum-shaped walls were tested). Referring to FIG. 16, Table 4, the relationship between the angle of the frustum-shaped wall and pressure characteristics is shown. Experimentation with various conical frustum shaped walls revealed that a desirable pressure characteristic (reduction in pressure fluctuation) increased as the frustum-shaped walls were angled up to 4 degrees from the central axis and then desirable characteristics began to diminish during the further increase up to 7 degrees. When the wall was configured at an angle x greater than 7 degrees away from the central axis, the air began to buffet, producing unacceptable pressure characteristics. Within the range of angles greater than 0 and less than 8 degrees from the central axis, it can be seen that the lowest fluctuations from high to low pressure during the breathing cycle were obtained utilizing a frustum-shaped wall angled at 4 degrees from the central axis.

In order to optimize the position of the jet (108) and the size of the jet orifice (110), experimentation was performed utilizing a right circular conic frustum-shaped wall with angle x (634) of 4 degrees and an 11 mm diameter circular patient end opening (104).

With minimal initial experimentation regarding the placement of the jet (108), it became immediately obvious that the highest static pressures per unit of supplementary gas used would be obtained where the jet orifice (110) was located approximately along the central axis (122, 626) of the frustum-shaped wall (102, 632), relatively near to the patient end opening (104, 622) and directed towards the patient end opening (104, 622) such that, in use, some portion of the gas flow would be oriented directly towards the patient end opening (104, 622) without impinging on the frustum-shaped wall (102). Off-center placement of the jet (108) (i.e. not along the central axis (122)) yielded functional but less efficient devices. Placing the jet (108) a great distance away from the patient end opening (104) yielded inefficient devices with little CPAP produced per amount of supplementary gas utilized. And not orienting the jet (108) substantially directly towards the patient end opening (104) also yielded inferior results. This last point in particular distinguishes the present invention from prior art disclosures, such as those by Boussignac referred to above, which teach the requirement of a deflection face as a means to deflect the jet(s) before the supplementary gas flows onward towards the patient end of the device.

Tests were performed using 3 different diameter circular jet orifice (110) sizes: 0.58 mm, 0.65 mm and 0.79 mm diameter. The gas flow was adjusted to maximum flow rate using a 50 PSI industry standard gas supply for each diameter jet orifice (110). For the 0.58 mm diameter orifice, the flow rate was 12.0 LPM, for the 0.65 mm diameter orifice, the flow rate was 13.0 LPM, and for the 0.79 mm diameter orifice, the flow rate was 18.0 LPM. Each of these 3 jet orifice sizes was also tested at various distances from the patient end opening (104). And this testing was performed with 4 different size cylindrical-walled prototypes as well as with 3 different size prototypes with frustum-shaped walls. Referring to FIGS. 17, 18 and 19, some of the significant results of this experimentation are tabulated in Tables 5, 6, and 7. Examining Tables 5, 6 and 7, one can see the results of many different parameter shifts upon static pressure and fluctuation. Although there are many possible workable choices revealed by the information expressed in these charts, applicant has selected for his examples below, an 11 mm diameter round patient end opening surrounded by a conical frustum-shaped wall with a wall angle of 4 degrees to the central axis, a jet with a 0.65 mm diameter jet orifice, located at 47 mm along the central axis from the patient end opening. As can be seen from table 6, this choice yields a static pressure of 9.5 mm H2O with a fluctuation of only 1.5 mm H2O throughout the breathing cycle while using only 13 LPM of supplementary gas.

The performance of commonly used CPAP devices is disclosed in an article titled Pneumatic Performance of the Boussignac CPAP System in Healthy Humans, by Maria Sehlin, et al. Commonly used devices such as the 10-57003 Mercury Flow-Safe CPAP system or the 5570.13 Boussignac CPAP device require 25 liters per minute of oxygen to generate 8.5 to 10 Cm H2O CPAP pressure. Referring to FIGS. 20 and 21, comparisons between applicant's invention and these 2 other prior art devices are tabulated in tables 8 and 9. Applicant's invention only requires approximately 12.5 liters per minute (50% of previously required flow) to generate the same CPAP pressure. Further, where each of the devices is tested at a flow rate that produces 10 cm H2O static pressure, the pressure fluctuation within either the 10-57003 Mercury Flow-Safe CPAP system or the 5570.13 Boussignac CPAP device is approximately twice that of the present invention.

Based on the above data, applicant has designed an optimized device. Referring to FIG. 1, a cross-section of one embodiment of the present invention is shown (100). The concave frustum-shaped wall (102) terminates at its narrow end with an 11 mm diameter circular patient end opening (104). The frustum-shaped wall (102) makes an angle of 4 degrees with its central axis (122). The patient end opening (104) leads directly into the universal connector (106) with 15.8 mm inner diameter. The connector (106) in this example is designed to be engaged indirectly with the breathing tract of a patient via a 15 mm female/22 mm male industry standard patient connection. This connector (106) may therefore be engaged with the external end of an endotracheal tube, a tracheostomy tube, mouthpiece, mask or the like, so that the device may be incorporated into the breathing path of a patient. However, the connector (106) may also be designed to engage with the patient's breathing tract directly if desired. Alternatively, the patient end opening (104) could be designed to connect directly to other equipment.

The jet (108) is located along the central axis of the concave frustum-shaped wall (102) and directed along the central axis (122) towards the patient end opening (104), with the jet orifice (110) located at 47 mm from the patient end opening (104). The jet orifice (110) has an inner diameter of 0.65 mm. In use, the jet (108) is supplied supplementary respirable gas from a respirable gas source (not shown) via the gas input port (112). The concave frustum-shaped wall (102) defines a frustum-shaped interior space (114). This example (100) has a concave conical frustum-shaped wall (102), approximately 47 mm in length measured along the frustum's central axis and with an interior diameter that varies from approximately 11 mm at the patient end opening (104) (i.e narrow end of frustum) to 17.5 mm at its wide end (120). The frustum-shaped wall (102,632) makes an angle x of approximately 4 degrees with the central axis (122, 626) of the corresponding frustum (620).

Figure 2:
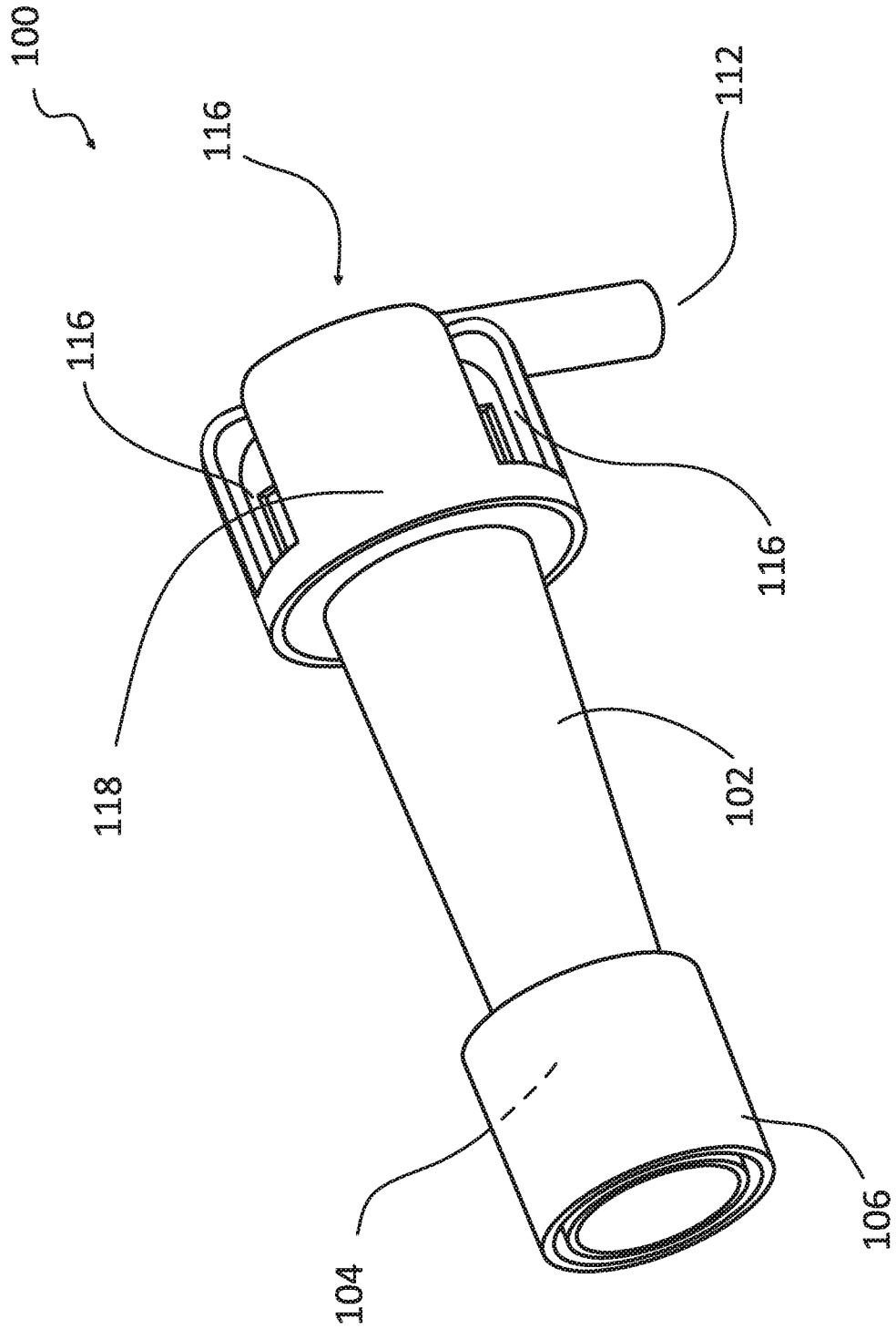
FIG. 2 shows an isometric view of an example of a breathing assistance device according to the present invention.

In this example, an endcap structure (118) provides housing and support for the jet (108) and the gas input port (112). The interior space (114) is in fluid communication with the atmosphere via 3 atmospheric openings (116) through the endcap structure. Referring to FIG. 2, the location of the 3 atmospheric openings (116) is illustrated. Applicant defines "fluid communication" as to include movement through a valve, a filter, or the like, or any other arrangement which allows substantially unimpeded exchange of gas between the interior of the device and the atmosphere.

The jet (108) also exhibits a concave frustum-shaped wall in its interior, that varies from 3 mm diameter at the point of connection to the gas input port (112) to 0.65 mm diameter at the jet orifice (110). The jet (108) is 19.8 mm long measured axially. The internal frustum-shaped wall of the jet (124) makes an angle of 3.4 degrees with the central axis (122) of the jet.

The above detailed measurements describe a non-limiting example and the device may of course be of any suitable size, shape and configuration within the spirit of the invention.

In use, supplementary respirable gas is directed through the jet (108) out the jet orifice (110) through the interior space (114) towards the patient end opening (104). The jet (108) creates an increased pressure, particularly near the patient end opening (104) and through the connector (106) and into the patient's airway. Upon inhalation, the patient breathes in supplementary respirable gas that enters the interior space (114) through the jet orifice (110) as well as atmospheric air that is drawn into the interior space (114) though the atmospheric openings (116). Upon exhalation, the expired air exits from the patient through the connector (106), out through the patient end opening (104), out through the interior space (114), and finally exiting the device (100) through the atmosphere openings (116).

The input port (112) of this embodiment is designed to be engaged via a standard connecting tube (not shown) with a source of supplementary respirable gas (not shown). The pressure delivered to the patient at any given moment will be dependent upon the pressure of the respirable gas entering the interior space (114) via the jet (108) as well as upon the transient flows of gas due to the patient's inhalation and exhalation through the interior space (114) during respiration. With an appropriate pressure from the supplementary respirable gas source, CPAP (continuous positive airway pressure) is produced for the patient. At lower pressures from the supplementary respirable gas source, a more passive supplementation of respirable gas may be provided to the patient. The flow of supplementary respirable gas through the jet, and the resulting pressure within the device, may be controlled externally with a flow meter, a pressure regulator, or the like.

Figure 7:
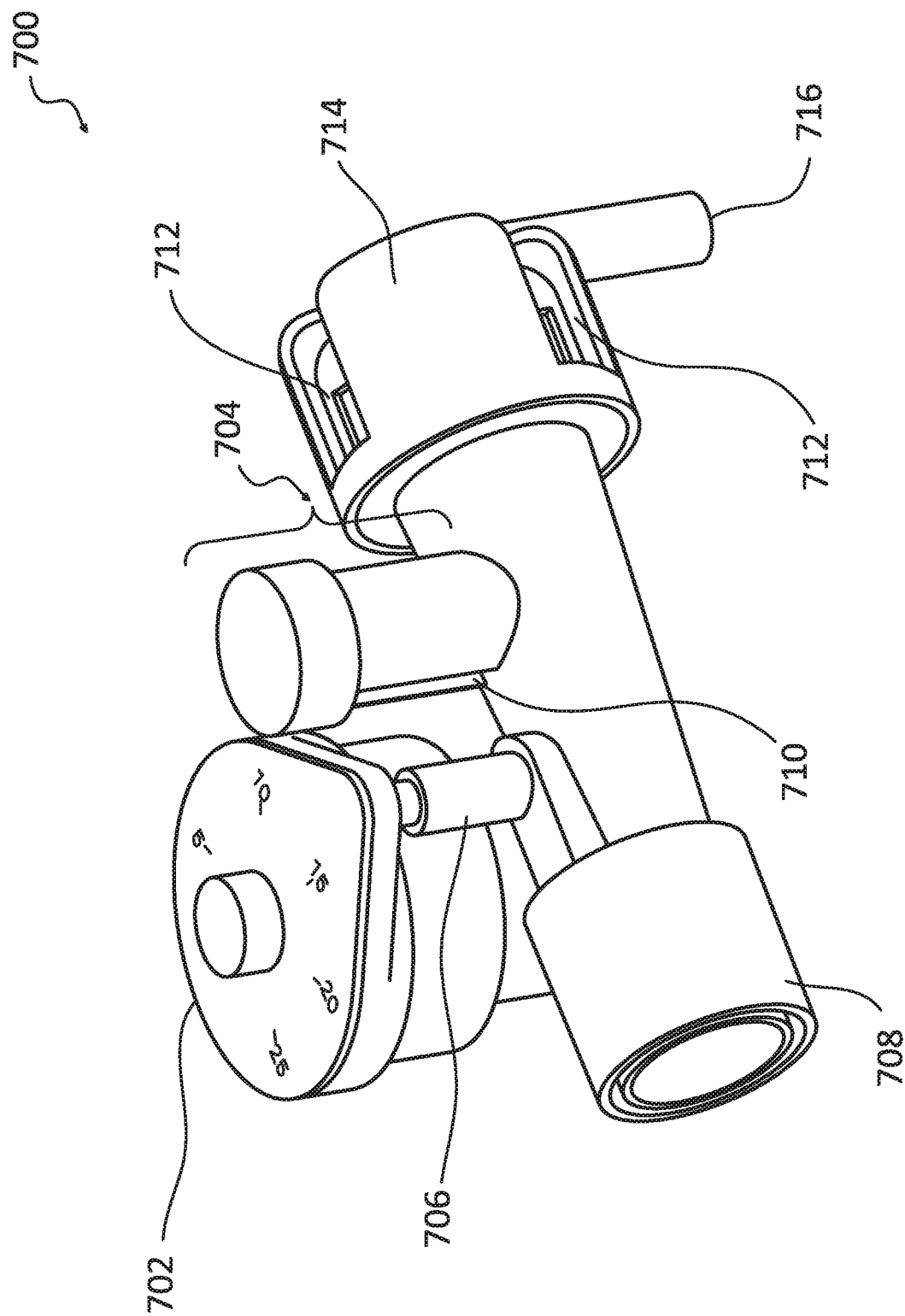
FIG. 7 shows an isometric view of an example of a breathing assistance device with manometer and pressure relief valve according to the present invention.
Figure 8:
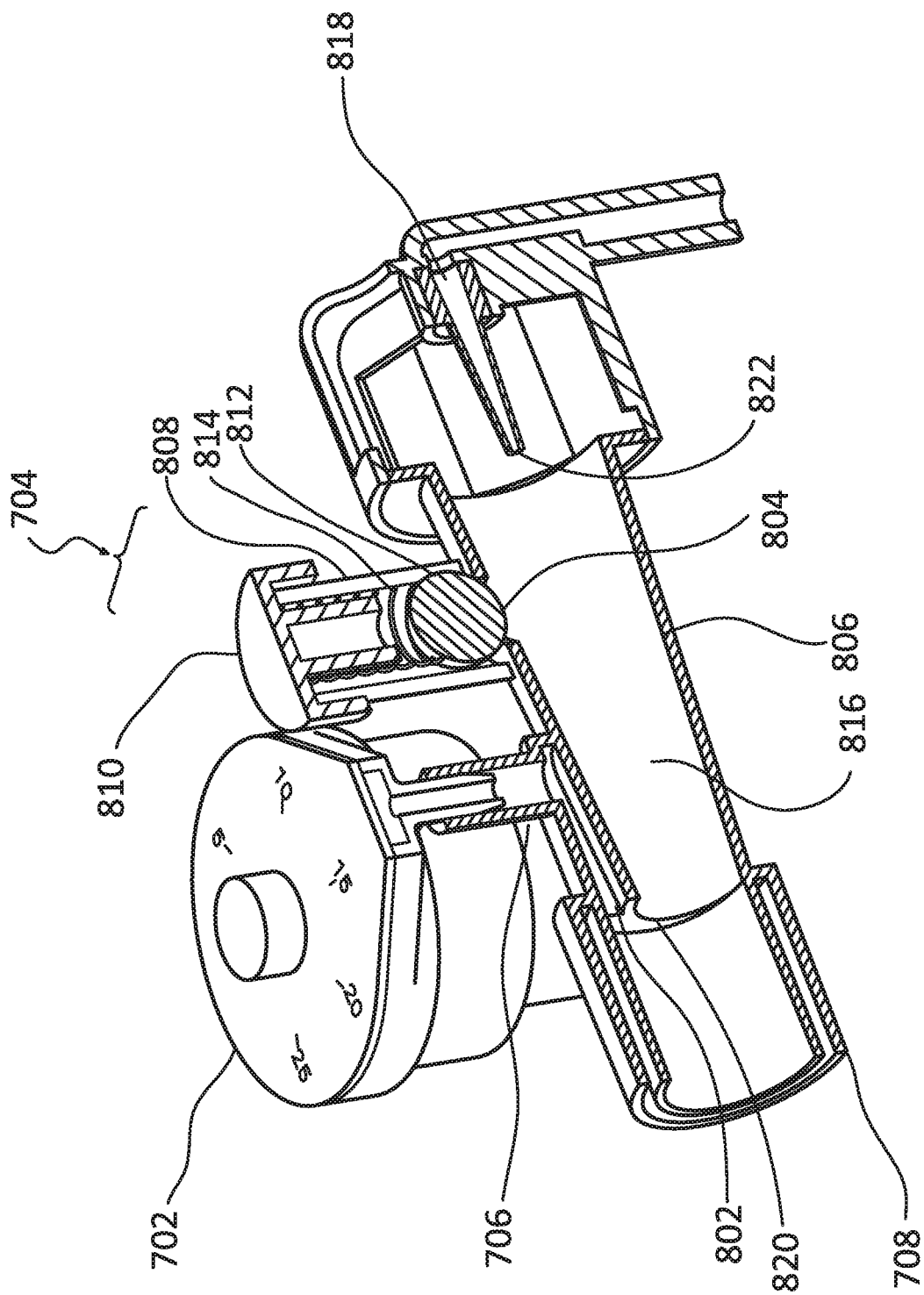
FIG. 8 shows an isometric section view of an example of a breathing assistance device with manometer and pressure relief valve according to the present invention.
Figure 9:
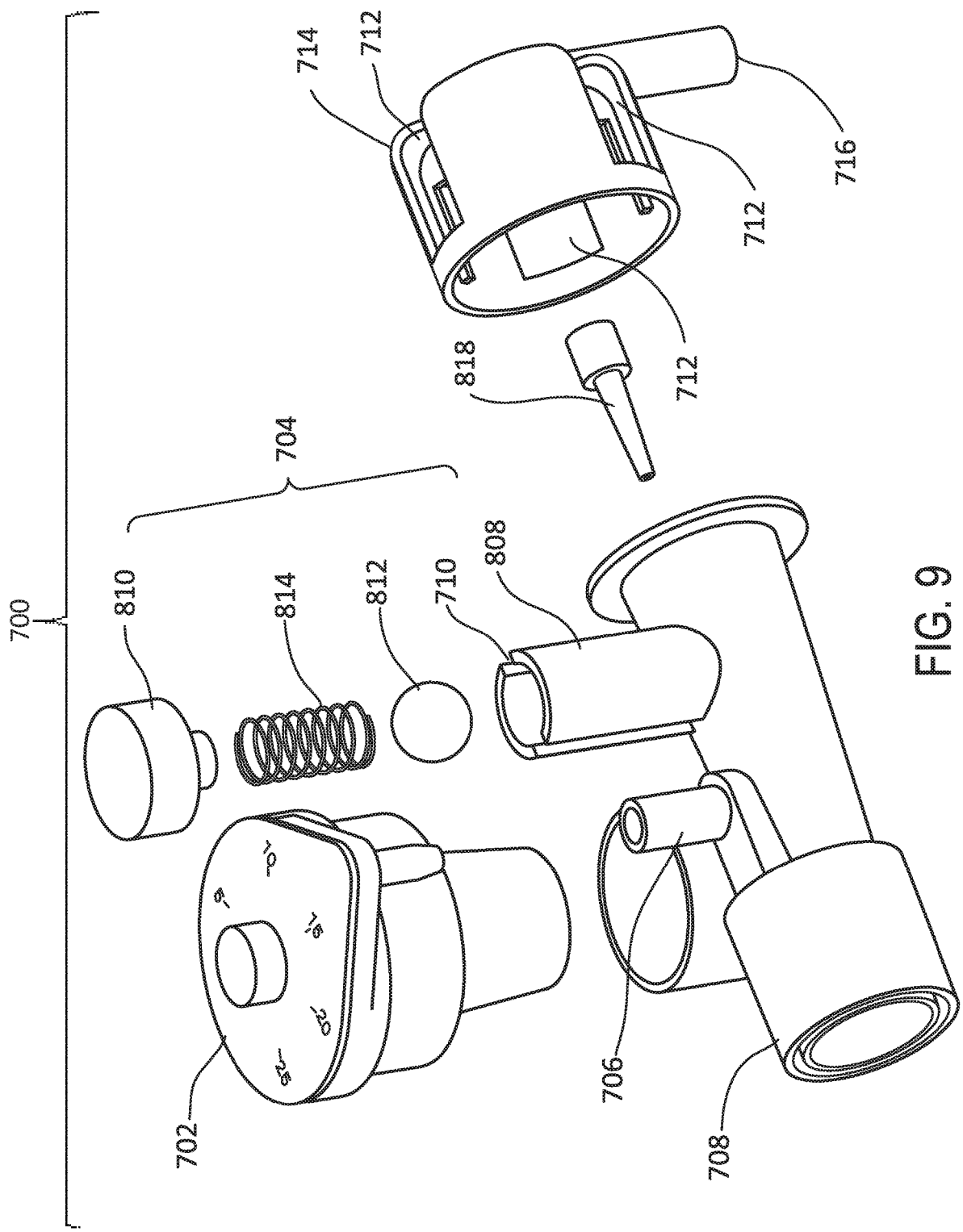
FIG. 9 shows an isometric exploded view of an example of a breathing assistance device with manometer and pressure relief valve according to the present invention.

Referring to FIGS. 7, 8 and 9, a second example of the present invention (700) has essentially the same structure as the example above (100) but further comprises a manometer (702) and a pop-off safety relief valve (704). The structure of the example (100) has been modified to include a manometer port (706) for attaching a manometer (702), disposable or otherwise, to measure the pressure just beyond the patient end opening (820) within the connector (708) via the pressure measurement channel (802). The sensing port of a disposable manometer (702) may be press fit, glued or otherwise firmly seated to the manometer port (706). The manometer (702) gives a continuous immediate display of the pressure inside the connector (708) near the patient end of the device (700). The currently described and illustrated configuration provides a readily discernible display directly on the side of the device. Such a prominent and easily perceived indication of internal pressure provides both convenience for one monitoring and/or applying the device, as well as added safety for the patient.

This example (700) of the invention further comprises a ball and spring "pop-off" safety relief valve (704). A pressure relief throughhole (804) made through the concave frustum-shaped wall (806) of the device (700). A "pop-off" safety relief valve housing (808) with pop-off housing endcap (810) encases the ball (812) and spring (814) mechanism and is attached to the outer surface of the frustum-shaped wall (806) covering the throughhole (804) such that the spring (814) presses the ball (812) into the throughhole (804) through the frustum-shaped wall (806), blocking gas from escaping through the throughhole (804). The spring (814) is calibrated such that it holds the ball (812) in position blocking the throughhole (804) until a threshold pressure is reached within the interior space (816). When the pressure within the interior space (816) rises to or above the threshold pressure, the spring (814) is compressed as the ball (812) is pushed away from the throughhole (804) by the pressurized gas within the interior space (816), allowing gas to escape the interior space (816) and out through the 2 pressure release vents (710) in the side of the "pop-off" safety relief valve housing (808), thereby decreasing the excess pressure within the interior space (816).

An example of an appropriate threshold pressure for CPAP application of a device constructed according to this example would be 25+/−5 cm H2O, but an appropriate range might be anywhere from 15 to 45 cm H2O depending upon preference and application. Thus, a safety pressure relief is provided in the case of overpressure within the interior space (816) e.g. because the atmospheric openings (712) are blocked by an obstruction, etc. This safety pressure relief valve (704) affords an added measure of safety for the patient. However, the atmospheric openings (712) are positioned around the sides and proximal surface of the end cap (714) such that the likelihood of an object inadvertently obstructing the fluid communication path between the interior space (816) and the atmosphere is decreased.

The "ball and spring" mechanism (704) placed as described above is a non-limiting example of a pressure relief mechanism. Other types of safety pressure relief mechanisms known in the art may be used, such as for example, a safety sleeve as described in U.S. Pat. No. 5,036,847. Even an open hole might be utilized to afford additional protection from overpressure to the patient. There are, of course, numerous other possibilities that could be employed within the scope of the invention. And any such pressure relief mechanism could likewise be placed in alternative locations within the device (700) to provide an additional safety pressure relief in the event of overpressure within the interior space (816) of the device.

The input port (716) of this embodiment is designed to be engaged via a standard connecting tube (not shown) with a source of supplementary respirable gas (not shown). The pressure delivered to the patient at any given moment will be dependent upon the pressure of the respirable gas entering the interior space (816) via the jet (818) as well as upon the transient flows of gas due to the patient's inhalation and exhalation through the interior space (816) during respiration. With an appropriate pressure from the supplementary respirable gas source, CPAP (continuous positive airway pressure) is produced for the patient. At lower pressures from the supplementary respirable gas source, a more passive supplementation of respirable gas may be provided to the patient.

The dimensions of the breathing assistance device with manometer and with pop-off safety relief valve (700) are similar to those of the first example (100) above. The manometer (702) and pop-off safety relief valve (704) can be included with minimal incursion into the interior space (816) and minimal distortion of the frustum-shaped wall (806). A 7 mm diameter throughhole (804), which is completely blocked by a portion of the ball's (812) surface, is all that is required for the pop-off safety relief valve while a pressure measurement channel (802) that opens into the interior space of the connector (708) is all that is required internally in order to allow successful pressure measurement via an attached manometer (702). Otherwise only external additions that do not encroach into the interior space (816), such as the manometer (702), the manometer port (706), the pop-off safety relief valve housing (808), the spring (814), and the pop-off safety relief valve endcap (810) are required.

The examples given above are meant to be non-limiting examples of ways to practice the current invention. Many varied embodiments may be conceived which fall within the scope and spirit of the present invention.

Variations

One definition of a frustum is "a truncated cone or pyramid in which the plane cutting off the apex is parallel to the base." Another definition is "the portion of a solid (normally a cone or pyramid) that lies between two parallel planes cutting it. The prototypes and examples discussed above comprise concave substantially frustum-shaped walls where the relevant frustum would satisfy either of the above definitions.

In constructing prototypes for these experiments only frustums of regular pyramids and right regular cones have been utilized by applicant. A regular pyramid is one whose base is a regular polygon whose center coincides with the foot of the perpendicular dropped from the vertex to the base. Applicant defines this perpendicular, dropped from the vertex to the base, as being the central axis of the frustums of right regular pyramids discussed herein. A right circular cone is a circular cone whose axis is perpendicular to its base. Applicant defines this axis as being the central axis for the frustums of right regular cones discussed herein.

Most generally, a frustum is "the portion of a solid (normally a cone or pyramid) that lies between two parallel planes cutting it." Another more limited definition of a frustum is "a truncated cone or pyramid in which the plane cutting off the apex is parallel to the base." Applicant defines the frustum of a regular pyramid as "the portion of a right regular pyramid included between the base and a section parallel to the base." Applicant defines the frustum of a right circular cone as "that portion of the right circular cone included between the base and a section parallel to the base."

We can readily interpolate from the results tabulated in FIG. 15 Table 3 that we could obtain desirable improvement in pressure characteristics with any regular polygonal wall, where n is greater than or equal to 4, by moving from a steady cross-sectional area type ("tubular") device to a device with a frustum-shaped wall of the corresponding type. If it works for a square, an octagon and a circle, as our experiments show, we can be quite certain it will work for any regular n-sided polygonal type wall where n is between 4 and infinity (the circle). We can also extrapolate that we will obtain similar improvement with a regular triangular pyramidal frustum-shaped wall as compared with the respective triangular tube.

Figure 10:
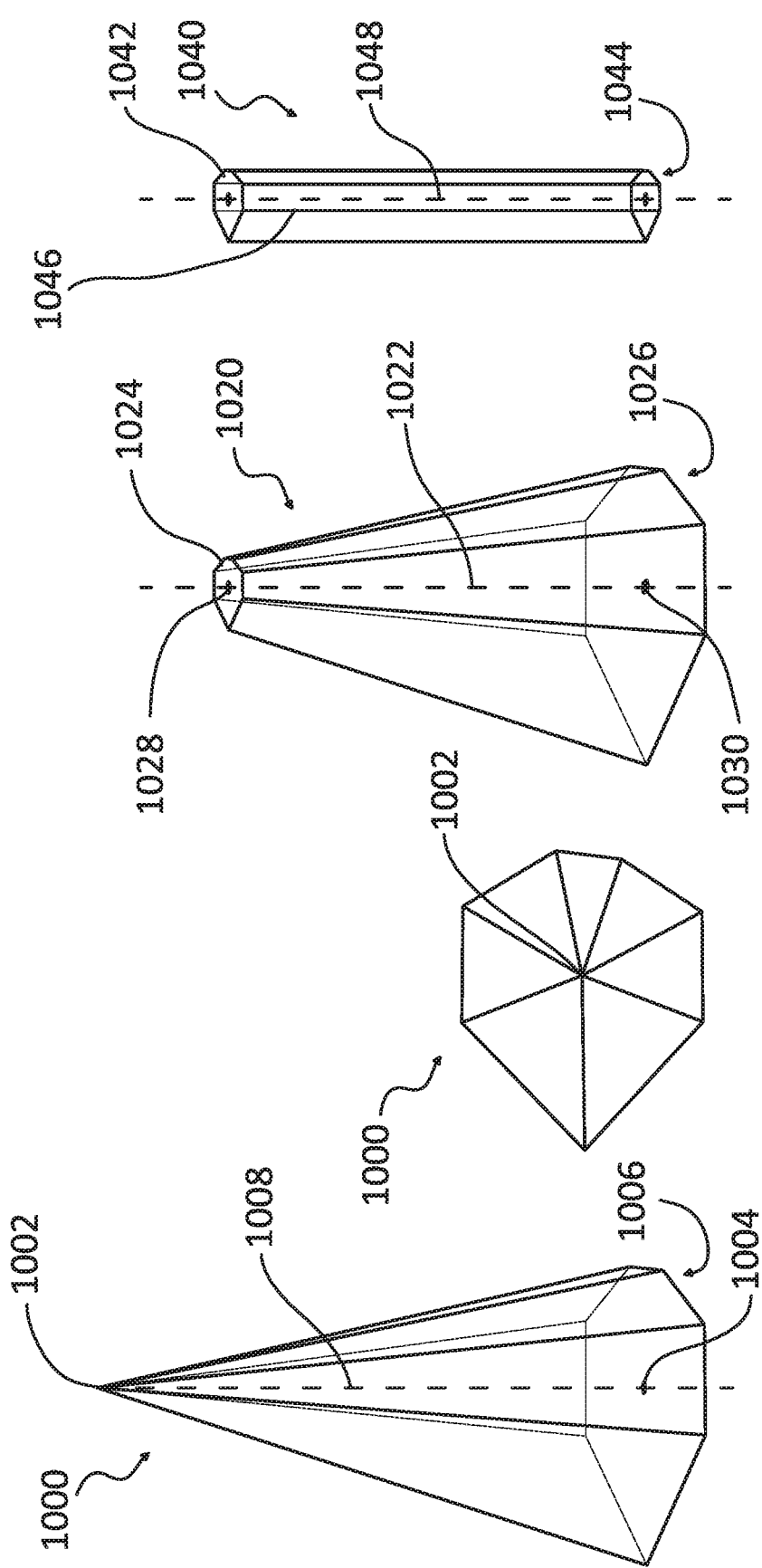
FIGS. 10A, 10B, 10C, and 10D compare an irregular heptagonal pyramid, an irregular heptagonal pyramidal frustum, and an irregular heptagonal tube.

And we can further assume that we would also obtain similar improvement by "angling out" the wall of many, if not all, steady cross-sectional area enclosing walls we might choose to surround the patient end opening (104). Referring to FIGS. 10A and 10B, a side view and a top view of an irregular pyramid (1000) are shown respectively. In this case, the vertex (1002) is located directly above the centroid (1004) of the base (1006) and the central axis (1008) is shown. In discussing right circular cones and regular pyramids, the geometric center of the base is easily located. Locating the centroid of an irregular polygon may be a bit more complicated.

Referring to FIG. 10C, a frustum (1020) of the irregular pyramid with central axis (1022) is shown. The top face (1024) of the frustum is an irregular heptagon as is the base (1026). The centroid (1028) of the top face (1024) as well as the centroid (1030) of the base (1026) are indicated. The central axis (1022) passes through these two points (1028, 1030).

Referring to FIG. 10D, an irregular "tubular" structure is shown. The top face (1042) and bottom face (1044) both have the exact same shape and dimensions as the top face (1024) of the irregular pyramidal frustum (1020). Any horizontal cross-section of the "tube" has the exact same shape and dimensions as the top face (1024) of the irregular pyramidal frustum (1020). Therefore the irregular tube (1040) defines a steady cross-sectional area throughout its length. If one were to construct 2 prototype breathing assistance devices; one having a concave frustum-shaped wall as in FIG. 10C (1020) with a patient end opening being the top face (1024), and the second prototype using the irregular tube-like structure (1040) represented in FIG. 10D; based on the data from applicant's experimentation as described above, we would expect better performance from a breathing assistance device which utilizes the frustum-shaped wall as in FIG. 10C, particularly if some side faces make an angle with the central axis (1022) of approximately 4 degrees.

And likewise we would anticipate achieving some measure of improvement by angling out some portion less than the entire enclosing wall. In other words, if we began with a tubular structure such as is represented in FIG. 10D (1040), and angled some but not all of the side faces (1046) away from what would be the patient end opening (1042) at an angle greater than 0 degrees and less than 8 degrees from the central axis (1048), some measure of improvement over the straight tubular structure (1040) would still be expected in this application. An infinite number of irregular pyramidal or deformed conic structures of this type could be readily conceived and we would anticipate improvement where we move from a tubular-type structure (at 0 degrees with respect to the central axis and defining a steady cross-sectional area along its length) to a structure with some portion of the wall surrounding the patient end opening angled away from the opening at greater than 0 degrees and less than 8 degrees. In other words applicant asserts that if there is a cross-section through the wall surrounding the patient end opening and which includes the central axis, where the wall surrounding the patient end opening makes an angle of more than 0 and less than 8 degrees with the central axis, then improvement in desired pressure characteristics would be expected over the comparable "tubular" structure.

Further, the concave frustum-shaped wall (102, 806) need not be completely symmetrical, smooth or regular. The substantially frustum-shaped wall may include reservoir areas, bends, curves, texturing, etc. as desired, while still remaining within the scope of the present invention. And thus the present inventive concept of obtaining improved CPAP pressure characteristics by utilizing angled walls surrounding the patient end opening, as opposed to utilizing a wall that defines interior space with a steady cross-sectional area, can be applied in many varied ways to an infinite number of differently shaped bodies in order to accomplish application of the present invention.

The examples above utilize a fully rotationally symmetric conic frustum-shaped wall (102, 806) with the patient end opening (104, 820) leading directly into a slightly tapered, substantially straight connector (106, 708) creating a very efficient streamlined structure which results in highly efficient performance. However, the invention can clearly be practiced in many and varied ways, most obviously with any regular polygonal pyramidal frustum-shaped wall, as well as with irregular concave frustum-shaped walls.

Although the above examples illustrate the connector (106, 708) being an Industry Standard Patient Connection designed to be engaged with a standard connector (for attachment to a mask, an endotracheal tube, etc.), the connector (106, 708) may alternatively be molded to any desired shape and size for the purpose of engaging with the breathing tract of the patient. For example, the connector (106, 708) may be molded into a mask, a mouthpiece, an endotracheal tube, etc. The connector (106, 708) may be straight, curved, narrow, wide, etc., and have whatever type of internal and external architecture that is preferred. Or one might choose to make the patient end opening (104, 820) of the frustum-shaped wall somewhat wider and then narrow the gas-flow path to a smaller cross-section within the connector (106, 708). A configuration such as this might take on many forms and still remain within the scope of the present invention.

Figure 11:
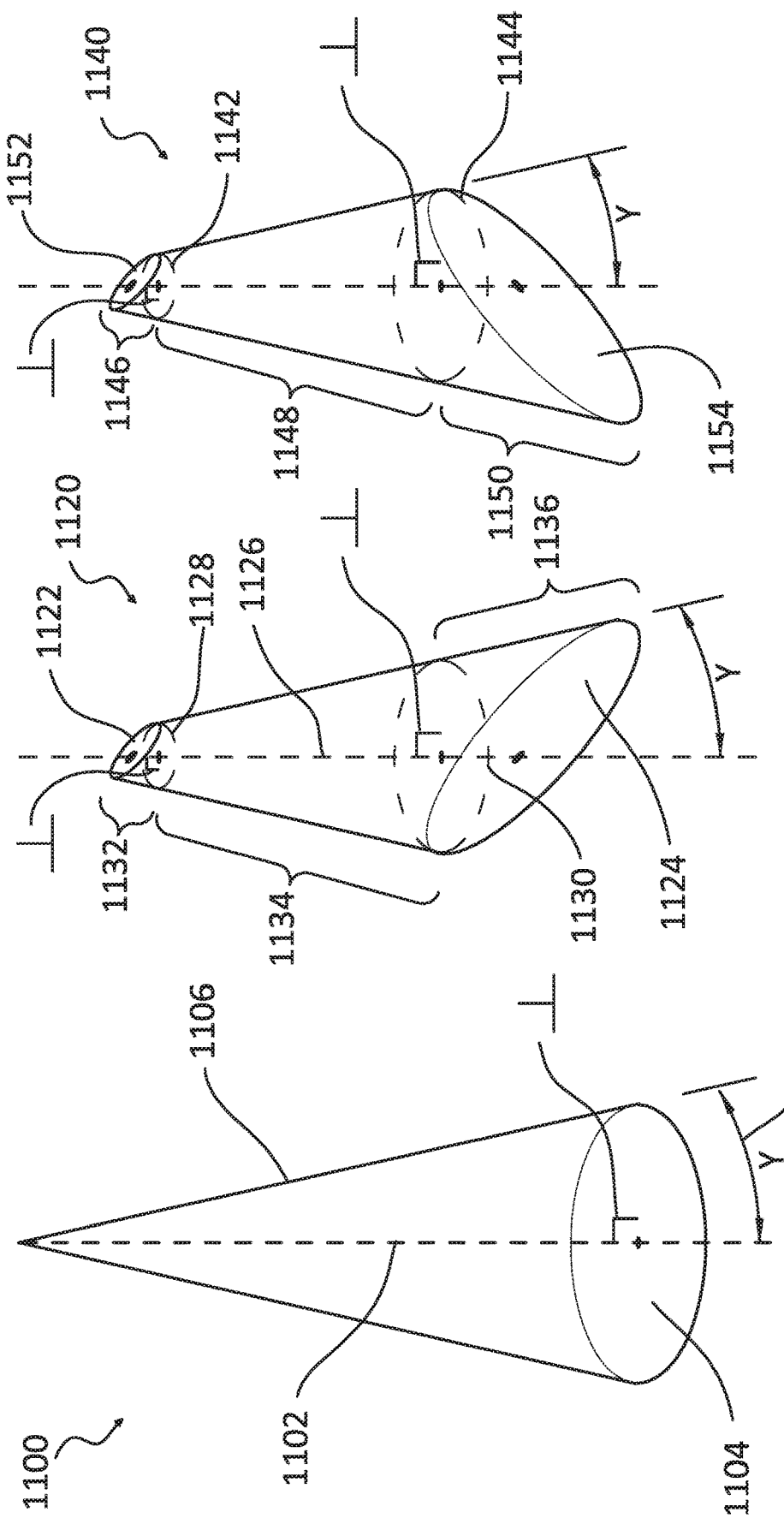
FIGS. 11A, 11B, and 11C compare a right circular cone, conic frustums and conic portions.

Referring to FIG. 11A, a right circular cone with central axis (1102) is shown (1100). The cone has a base (1104) and sidewall (1106). The sidewall (1106) makes angle y (1108) with the central axis (1102). Referring to FIG. 11B, a frustum (1120) of the same cone (1100), according to a more general definition of frustum, is shown. The frustum has an elliptical top face (1122) and a parallel elliptical bottom face (1124), each making congruent angles with the central axis (1126) of the corresponding cone (1100). Cutting cross-sections (1128,1130) through the frustum (1120) perpendicular to the axis (1126) of the corresponding right circular cone divides the structure into 3 portions, a top segment (1132), a middle portion (1134) and a bottom portion (1136). The middle portion (1134) resulting from this division is a frustum of a right circular cone with the same central axis (1126) as the corresponding cone (1100).

One might desire to use a wall with a shape (1120) such as that shown in FIG. 11B to practice the present invention. However, the geometry reveals that this shape (1120)

reduces to a middle frustum-shaped portion (1134) and top and bottom portions (1132, 1136). In such a case, the top smaller circular face (1128) of the frustum-shaped middle portion (1134) could be considered to be the concave frustum-shaped wall with central axis (1126), while the top portion (1132) could be considered to be part of the connector (106, 708). The lower portion (1136) might have little to do with the pressure characteristics of the device especially if it is located further away from the patient end opening (104, 820) than the jet orifice (110, 822).

Referring to FIG. 11C, a portion of a right circular cone is shown (1140). Unlike FIG. 11B, this portion (1140) is not a frustum even according to the most general definition. However, as in the previous example, this shape (1140) may be divided with cross-sections (1142, 1144) parallel to the base (1104) of the corresponding right circular cone (1100) to yield a middle frustum-shaped portion (1148) and top and bottom portions (1146, 1150). As in the above example, if one desired to use a shape such as that represented here (1140) to construct a breathing assistance device according to the present invention, the middle portion (1148) could be viewed as the frustum-shaped wall with patient end opening (1142) while the top portion (1146) could be viewed as part of the connector (106, 708). Again, the lower portion (1150) might have little to do with the pressure characteristics of the device especially if it is located further away from the patient end opening (104, 820) than the jet orifice (110, 822).

The same mathematical logic can be applied similarly to reduce irregular pyramidal type shapes.

Figure 12:
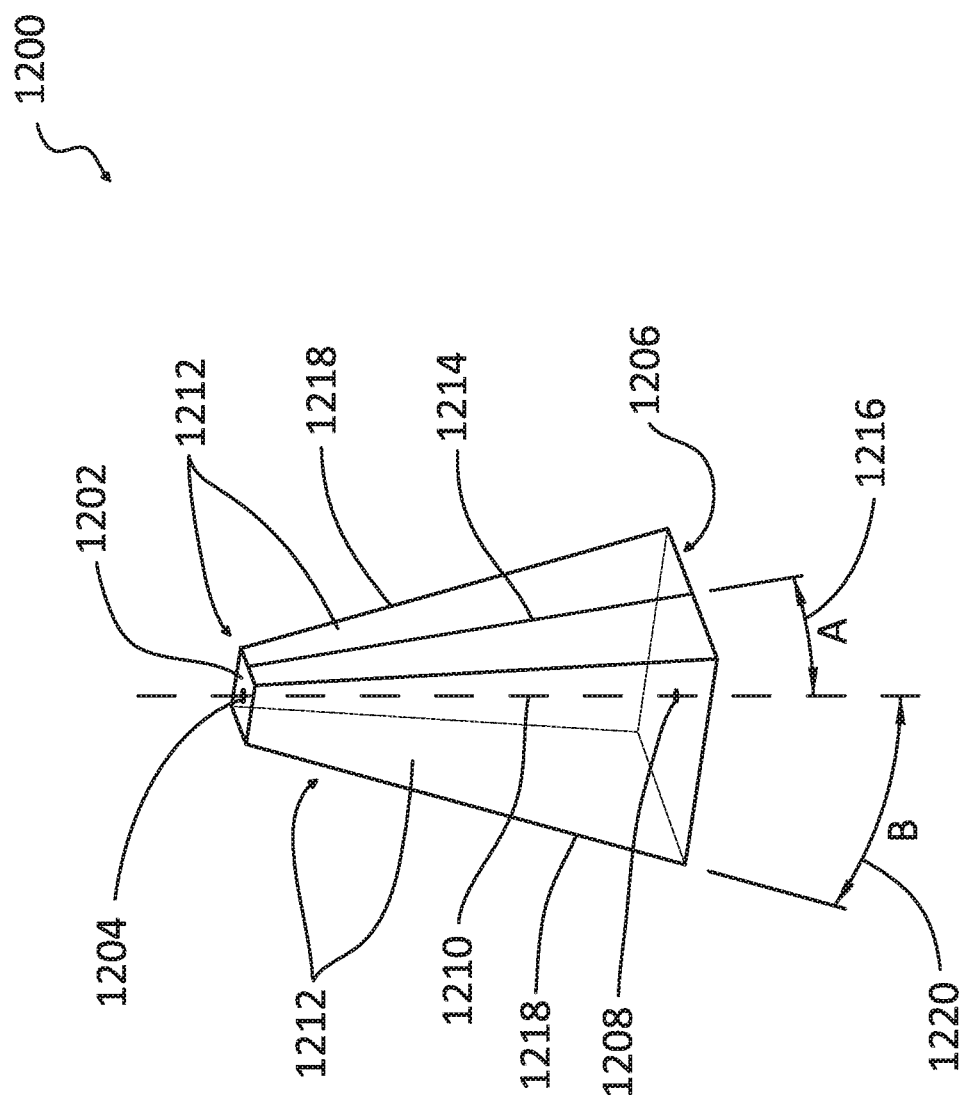
FIG. 12—Illustrates the variation of the angle between the central axis and various locations on a side face of a pyramidal frustum.

FIG. 12 illustrates the variation of the angle between the central axis and various locations on a side face of a pyramidal frustum. Referring to FIG. 12, a frustum (1200) of a regular square pyramid is shown. The frustum (1200) has a square top face (1202) with center (1204) marked and a square bottom face (1206) with center (1208) marked. The central axis (1210) runs through the center (1204) of the top face (1202) and the center (1208) of the bottom face (1206). The frustum has 4 side faces (1212). A line (1214) drawn down the center of a side face (1212) makes angle A (1216) with the central axis (1210). The frustum also has 4 edges (1218) where the side faces (1212) meet each other. A side edge (1218) of a side face (1212) of the frustum (1200) forms angle B (1220) with the central axis (1210). We can see that angle B (1220) and angle A (1216) are not equivalent and that angle B (1220) is greater than angle A (1216). For example, where angle A (1216) is 4 degrees, angle B (1220) is 5.65 degrees.

This illustrates that when dealing with non-conic frustums (e.g. 420, 520, 1020, 1200) the angle made between the frustum wall and the central axis will vary depending upon where on the wall the measurement is made. The frustum of the right circular cone (620) is the special case where the wall of the frustum (632) makes a constant angle with the central axis (626) no matter where around the perimeter (circumference) of the wall one measures.

In the above examples, the primary component pieces are from molded polycarbonate plastic. However, plastic formed in this manner is a non-limiting example of a suitable material and the device may be fashioned from any suitable materials, for example styrene, acetal, polypropylene, PVC, etc. Likewise, the pressure relief spring (814) is made from stainless steel but could be fashioned from any flexible metal, plastic or rubber.

In the above examples, the gas input port (112, 716) is an integrally molded feature of the end cap (118, 714). The manometer port (706) is an integrally molded feature of the main body of the device (700). But alternatively, each could be separate pieces attached by adhesive, mechanical fastening, ultrasonic welding, etc.

In the above examples, the inlet of the manometer pressure measurement channel (802) is located just beyond the patient end opening (820) within the connector (708) and the manometer port (706) is located approximately one third of the way along the length of the frustum-shaped wall (806) from the patient end opening (820). This is a non-limiting example of the placement of the manometer channel (802) and port (706). A disposable manometer (702) and a pressure tap (802) could be placed in any suitable desired location in fluid communication with the industry standard patient connection (708). And likewise, the manometer (702) may be of the design described in U.S. Pat. No. 5,557,049, by Ratner, or of any other suitable manometer design.

In the above examples, atmospheric openings (116, 712) of the device are left open to the atmosphere. However, the atmospheric openings (116, 712) need not be left wide open in order for the interior space to be in fluid communication with the atmosphere. For example, a filter could be placed within, over, or within an extension of the end cap (118, 714) while still retaining the desired characteristic of fluid communication of the interior space (114, 816) with the atmosphere, allowing for exhalation out through the atmospheric openings (116, 712), release of excess pressure, as well as influx of fresh atmospheric air into the device. Likewise, other devices that allow fluid communication of the interior space (114, 816) with the atmosphere through the atmospheric openings (116, 712) could be placed within, over, or as extensions of the atmospheric openings (116, 712) while still allowing the desired function.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

I claim:

1. A breathing assistance device comprising:
a body having an inside wall that is frustum-shaped;
said inside wall defining an interior space;
said inside wall having a narrow end and a wide end and a central axis;
said narrow end of said inside wall forming a patient end opening;
said patient end opening leading to a connector, said connector adapted to be engaged directly with a patient's breathing tract or adapted to be engaged indirectly with the patient's breathing tract;
a manometer, the manometer in fluid communications with the connector:
said body having a distal end portion distal from the wide end of the inside wall, the distal end portion comprising a nozzle and an annular wall, wherein the annular wall surrounds the nozzle, and the annular wall comprises a plurality of openings placed along an annular surface of the annular wall, the plurality of openings are configured to allow fluid to communicate between the interior space and an atmosphere; and said nozzle having a jet orifice and is adapted to be supplied with supplementary respirable gas by a respirable gas source, the jet orifice directing the supplementary respirable gas directly into the wide end of the inside wall and through said interior space substantially along said central axis of the inside wall towards said patient end opening; wherein the inside wall is continuous between the jet orifice and the patient end opening; and wherein the inside wall is successively narrower towards the patient end opening.

2. The breathing assistance device according to claim 1, where said inside wall has a rectangular cross-sectional shape.

3. The breathing assistance device according to claim 1, where said inside wall is substantially a square pyramidal-shaped wall or substantially an octagonal pyramidal-shaped wall.

4. The breathing assistance device according to claim 1, where said inside wall diverges at an angle greater than 0 and less than 4 degrees from said central axis thereof.

5. The breathing assistance device according to claim 1, where said inside wall diverges at an angle greater than 3 degrees and less than 4 degrees from said central axis thereof.

6. The breathing assistance device according to claim 1, where said inside wall diverges at an angle of 4 degrees from a lengthwise axis of the interior space.

7. The breathing assistance device according to claim 1, where said patient end opening has a cross-sectional area between 65 and 185 square millimeters.

8. The breathing assistance device according to claim 1, where said patient end opening has a cross-sectional area of 95 square millimeters.

9. The breathing assistance device according to claim 1, where a gas flow path through said connector is restricted to a cross-sectional area between 63 and 185 square millimeters.

10. The breathing assistance device according to claim 1, where a distance of the jet orifice from the patient end opening is between 25 and 70 millimeters.

11. The breathing assistance device according to claim 1, where a distance of the jet orifice from the patient end opening is 47 millimeters.

12. The breathing assistance device according to claim 1, where the jet orifice has a diameter of between 0.5 and 1.0 millimeters.

13. The breathing assistance device according to claim 1, where the jet orifice has a diameter of 0.65 millimeters.

14. The breathing assistance device according to claim 1, where said breathing assistance device is disposable.

15. The breathing assistance device according to claim 1, further comprising a pressure relief valve in fluid communication with said interior space through a hole through the inside wall, the pressure relief valve having a ball that occludes the hole during inhalation, thereby preventing leakage through the hole.

16. A breathing assistance device comprising:
a body;
said body having an inside wall;
said inside wall having a narrow end and a wide end;
said narrow end of the inside wall forming a patient-end opening;
said patient-end opening having a centroid;
said wide end of said inside wall having a centroid;
said inside wall having a central axis, said central axis passing through said centroid of said patient-end opening and though said centroid of said wide end of said inside wall;
where there is a cross-section of said body which includes said central axis where said inside wall forms a linear angle greater than 0 degrees and less than 8 degrees with said central axis;
said inside wall defining an interior space;
a manometer, the manometer in fluid communications with the connector; said body having a distal end portion distal from the wide end of the inside wall, the distal end portion comprising a nozzle and an annular wall, wherein the annular wall surrounds the nozzle, and the annular wall comprises a plurality of openings placed along an annular surface of the annular wall, the plurality of openings are configured to allow fluid to communicate between the interior space and an atmosphere; and said nozzle adapted to be supplied with supplementary respirable gas by a respirable gas source, said nozzle directing the supplementary respirable gas directly into the wide end of the inside wall and through said interior space towards said patient-end opening; wherein the inside wall reduces in area linearly from an exit orifice of the nozzle to the patient-end opening; and wherein the inside wall is successively narrower towards the patient-end opening.

17. A breathing assistance device comprising:
a body exhibiting an inside wall that is continuously narrowing;
said inside wall defining an interior space;
said inside wall having a narrow end and a wide end and a central axis;
said narrow end of said inside wall forming a patient end opening; a manometer, the manometer in fluid communications with the connector; said body having a distal end portion distal from the wide end of the inside wall, the distal end portion comprising a nozzle and an annular wall, wherein the annular wall surrounds the nozzle, and the annular wall comprises a plurality of openings placed along an annular surface of the annular wall, the plurality of openings are configured to allow fluid to communicate between the interior space and an atmosphere; and said nozzle having a jet orifice, and adapted to be supplied with supplementary respirable gas by a respirable gas source and for directing supplementary respirable gas directly into said wide end of the inside wall and through said interior space substantially along said central axis of said inside wall towards said patient end opening; and
said breathing assistance device further comprising a connector and said connector adapted to engage said breathing assistance device with a patient;
wherein the inside wall is successively narrower towards the patient end opening.

18. A breathing assistance device comprising:
a body exhibiting a concave substantially frustum-shaped wall;
said substantially frustum-shaped wall defining an interior space;
said substantially frustum-shaped wall having a narrow end and a wide end and a central axis;
said narrow end of said substantially frustum-shaped wall forming a patient end opening;
a manometer, the manometer in fluid communications with the connector; said body having a distal end portion distal from the wide end of the inside wall, the distal end portion comprising a nozzle and an annular wall, wherein the annular wall surrounds the nozzle, and the annular wall comprises plurality of openings placed along an annular surface of the annular wall, the plurality of openings are configured to allow fluid to communicate between the interior space and an atmosphere; and said nozzle having a jet orifice, and adapted to be supplied with supplementary respirable gas by a respirable gas source, said nozzle directing supplementary respirable gas directly supplementary respirable gas directly into the interior space at the wide end of the substantially frustum-shaped wall and through said interior space substantially along said central axis of said frustum substantially frustum-shaped wall towards said patient end opening; and said breathing assistance device further comprising a connector and said connector adapted to engage said breathing assistance device with a patient.

\* \* \* \* \*